US009889229B2

(12) United States Patent
Gittens Ibacache et al.

(10) Patent No.: US 9,889,229 B2
(45) Date of Patent: Feb. 13, 2018

(54) SURFACE MODIFICATION OF IMPLANT DEVICES

(71) Applicant: Georgia Tech Research Corporation, Atlanta, GA (US)

(72) Inventors: Rolando A. Gittens Ibacache, Atlanta, GA (US); Jonathan Vernon, Atlanta, GA (US); Kenneth H. Sandhage, Atlanta, GA (US); Barbara D. Boyan, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 375 days.

(21) Appl. No.: 14/362,468

(22) PCT Filed: Dec. 7, 2012

(86) PCT No.: PCT/US2012/068469
§ 371 (c)(1),
(2) Date: Jun. 3, 2014

(87) PCT Pub. No.: WO2013/086336
PCT Pub. Date: Jun. 13, 2013

(65) Prior Publication Data
US 2014/0329052 A1 Nov. 6, 2014

Related U.S. Application Data

(60) Provisional application No. 61/568,869, filed on Dec. 9, 2011.

(51) Int. Cl.
*C23C 8/10* (2006.01)
*A61L 27/50* (2006.01)
*C23C 22/48* (2006.01)

(52) U.S. Cl.
CPC ........... *A61L 27/50* (2013.01); *A61L 2400/12* (2013.01); *A61L 2400/18* (2013.01); *A61L 2420/02* (2013.01); *Y10T 428/24355* (2015.01)

(58) Field of Classification Search
CPC .. A61L 27/50; A61L 2400/12; A61L 2400/18; A61L 2420/02; C23C 22/48; C23C 22/54
See application file for complete search history.

(56) References Cited

U.S. PATENT DOCUMENTS 4,200,474 A 4/1980 Morris
5,211,833 A 5/1993 Shirkhanzadeh
(Continued)

FOREIGN PATENT DOCUMENTS

WO WO 2008/154593 A1 12/2008
WO WO 2011094604 * 8/2011 ............... A61F 2/02

OTHER PUBLICATIONS

Extended European Search Report corresponding to European Application No. 11737768.9 issued Dec. 7, 2015.
(Continued)

*Primary Examiner* — Lois Zheng
(74) *Attorney, Agent, or Firm* — Myers Bigel, P.A.

(57) ABSTRACT

The present invention provides implant devices comprising nanoscale structures on the surface thereof and methods of manufacturing such implant devices. In some embodiments, methods of manufacturing an implant device comprise exposing a surface of the implant device to an oxidative hydrothermal environment for a duration sufficient to generate nanoscale structures on the exposed surface(s) of the implant device.

18 Claims, 23 Drawing Sheets

(56) References Cited

U.S. PATENT DOCUMENTS

| | | | |
|---|---|---|---|
| 5,320,686 | A | 6/1994 | Johansson et al. |
| 5,456,723 | A | 10/1995 | Steinemann et al. |
| 6,210,807 | B1 | 4/2001 | Dong et al. |
| 6,447,295 | B1 | 9/2002 | Kumar et al. |
| 7,938,855 | B2 | 5/2011 | Gregorich et al. |
| 8,052,744 | B2 | 11/2011 | Girton |
| 2002/0198601 | A1 | 12/2002 | Bales et al. |
| 2004/0153154 | A1 | 8/2004 | Dinkelacker |
| 2005/0113936 | A1 | 5/2005 | Brustad et al. |
| 2006/0116002 | A1 | 6/2006 | Kalkhoran et al. |
| 2006/0121080 | A1 | 6/2006 | Lye et al. |
| 2006/0246297 | A1 | 11/2006 | Sakoske et al. |
| 2007/0259427 | A1 | 11/2007 | Storey et al. |
| 2008/0274671 | A1 | 11/2008 | O'Donoghue et al. |
| 2008/0318044 | A1* | 12/2008 | Tian ............ A61L 27/06 428/401 |
| 2009/0220561 | A1 | 9/2009 | Jin et al. |
| 2009/0236014 | A1 | 9/2009 | Wilson et al. |
| 2009/0258327 | A1 | 10/2009 | Zipprich |
| 2009/0304772 | A1 | 12/2009 | Choubey et al. |
| 2013/0045360 | A1* | 2/2013 | Ibacache ........ A61F 2/30771 428/141 |
| 2013/0129788 | A1* | 5/2013 | Webster ........ A61L 27/22 424/400 |

OTHER PUBLICATIONS

Notification of Transmittal of the International Search Report and the Written Opinion of the International Searching Authority, or the Declaration corresponding to PCT Application No. PCT/US2011/023011 dated Apr. 7, 2011.
International Preliminary Report on Patentability corresponding to PCT Application No. PCT/US2011/023011 dated Jul. 31, 2012.
Notification Concerning Transmittal of International Preliminary Report on Patentability corresponding to PCT Application No. PCT/US2012/068469 dated Jun. 19, 2014.
Notification of Transmittal of the International Search Report and the Written Opinion of the International Searching Authority, or the Declaration corresponding to International Application No. PCT/US2012/068469 dated Apr. 12, 2013.
De la Hoz et al. "Microwaves in organic synthesis. Thermal and non-thermal microwave effect", *Chem. Soc. Rev.* 34:164-178 (2005).
Karthega et al, "In vitro studies of hydrogen peroxide treated titanium for biomedical applications", *Electrochimica Acta* 55:2201-2209 (2010).
Komameni et al, "Microwave-Hydrothermal Synthesis of Ceramic Powders", *Mat. Res. Bull.* 27:1393-1405 (1992).
Liu et al. "Surface nano-functionalization of biomaterials", *Materials Science and Engineering R*70:275-302 (2010).
Rohanizaden et al, "Preparation of different forms of titanium oxide on titanium surface: Effects on apatite depositions", *J Biomed Mater Res* 71A:343-352 (2004).
Wang et al. "Improvement of bioactivity of $H_2O_2/TaCl_5$-treated titanium after subsequent heat treatments", *J Biomed Mater Res* 52:171-176 (2000).
Wang et al. "In vitro bioactivity evaluation of titanium and niobium metals with different surface morphologies", *Acta Biomaterialia* 4:1530-1535 (2008).
Wiesbrock et al. "Microwave-Assisted Polymer Synthesis: State-of-the-Art and Future Perspectives", *Macromol. Rapid Commun.* 25:1739-1764 (2004).
Wu et al, "Preparation of photocatalytic anatase nanowire films by in situ oxidation of titanium plate", *Nanotechnology* 20:1-8 (2009).
Zhang et al. "In vitro and in vivo evaluation of SLA titanium surfaces with further alkali or hydrogen peroxide and heat treatment", *Biomed. Mater.* 6:1-7 (2011).
Zhang et al. "Effects of a hybrid micro/nanorod topography-modified titanium implant on adhesion and osteogenic differentiation in rat bone marrow mesenchymal stem cells", *International Journal of Nanomedicine* 8:257-265 (2013).

* cited by examiner c)

d)

a)

b)

a) Acid Treatment 3K X c) Caustic Treatment b) 20K X d)

Untreated sTiAlV

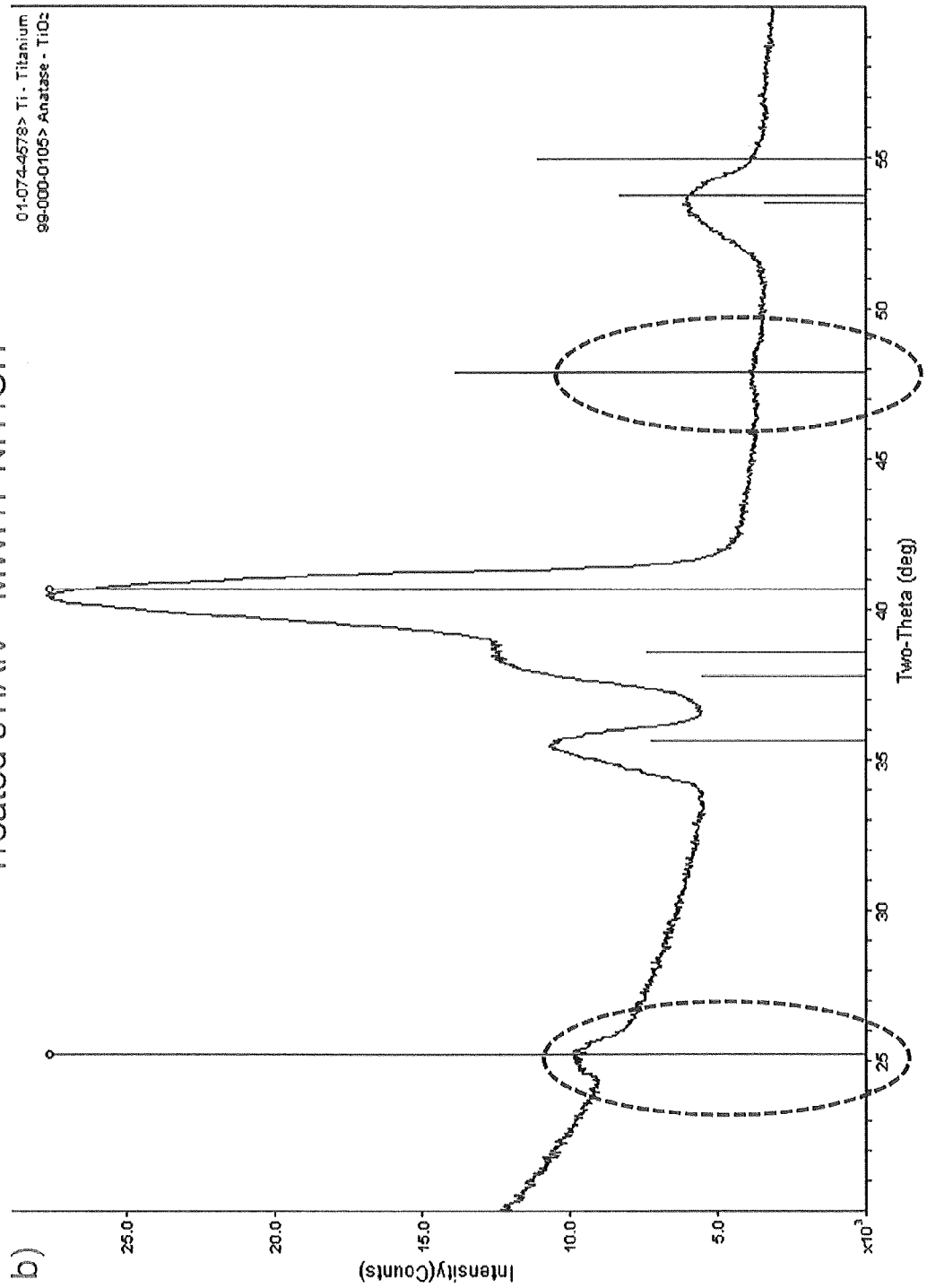

A

B

SURFACE MODIFICATION OF IMPLANT DEVICES

RELATED APPLICATIONS

This application is a 35 U.S.C. §371 national phase application of PCT International Application No. PCT/US2012/068469, having an international filing date of, Dec. 7, 2012 which claims priority to U.S. Provisional Application No. 61/568,869, filed on Dec. 9, 2011, the disclosures of which are hereby incorporated by reference herein in their entireties. The above-referenced PCT International Application was published as International Publication No. WO 2013/086336 A1 on Jun. 13, 2013.

FIELD OF THE INVENTION

The present invention relates to surface modification techniques and, more particularly, to surface modification techniques for biomaterials.

BACKGROUND

The aging U.S. population and the prevalence of musculoskeletal disease are driving efforts to take advantage of the regenerative properties of bone. Mesenchymal stem cells (MSCs) used as direct or indirect agents for regenerative therapies are an attractive approach because of their relative abundance in the body and ease of access. However, their effectiveness for bone regeneration relies on their differentiation state. Manipulation of MSCs towards osteoblastic lineage through surface structural cues has been suggested as an approach to improve clinical outcomes.

Micro- and submicro-structures on the surface of titanium alloy implants for dental and orthopedic applications have been shown to promote MSC differentiation into osteoblasts in the absence of external soluble factors in vitro and to improve osseointegration in vivo. See, e.g., Cochran et al., CLIN. ORAL IMPLANTS RES. 13:144 (2002); Olivares-Navarrete et al., BIOMATERIALS 31:2728 (2010); Wall et al., BONE 45:17 (2009).

Recently, we have developed technology for applying nanotexture to the surface of titanium-based implant devices using a gas/solid reaction at high temperatures. Gittens et al., BIOMATERIALS 32:3395 (2011). Using this method, nanoscale titania features of uniform roughness can be introduced over the entire surface of an implant device without altering the overall micro- and submicro-scale topography of the device. In vitro studies showing that osteoblastic differentiation is enhanced on these nanomodified surfaces, suggest that such in vivo osseointegration may be enhanced as well.

Because prior nanotexturing methods require the use of high temperatures (≥700° C.), which may degrade the mechanical performance of an implant device when placed in specific load-bearing functions, we sought to identify a method of forming microscale and/or nanoscale structures on the surface of implant devices using less heat.

SUMMARY OF THE INVENTION

The present invention provides devices comprising nanoscale structures on the surface thereof and methods of manufacturing such devices.

In some embodiments, the present invention provides a method of forming nanostructures on a surface of a device (e.g., an implant device), said method comprising exposing the surface of the device to an oxidative hydrothermal environment. The oxidative hydrothermal environment may comprise, consist essentially of or consist of an oxidizing solution that has been heated using microwave irradiation.

In some embodiments, the present invention provides devices (e.g., implant devices) comprising one or more nanostructures formed by a method of the present invention. The nanoscale structures may have an average diameter of about 1 to about 100 nm, an average height of about 10 to about 200 nm and/or a mean peak to valley height of about 1 to about 300 mm. The density of the nanoscale structures may be about 5 to about 10,000 per square micrometer.

BRIEF DESCRIPTION OF THE DRAWINGS

FIG. 2A shows the surface of the disk at 3,000× magnification. FIG. 2B shows the surface of the disk at 20,000× magnification.

FIG. 2C shows the surface of the disk at 3,000× magnification. FIG. 2D shows the surface of the disk at 20,000× magnification.

FIGS. 4A-4B are x-ray diffraction spectra of $Ti_6Al_4V$ samples (A) before and (B) after exposure to an oxidative hydrothermal environment (1 M $NH_4OH$ at 200° C. for 1 hour). The dashed ovals highlight the main differences between the spectrum of FIG. 4A and the spectrum of FIG. 4B, which are related to the presence of anatase peaks on the specimen exposed to an oxidative hydrothermal environment.

M H2O2 SLA"); 2 M $H_2O_2$ at 200° C. for 1 hour ("2 M H2O2 SLA"); and 2.5 M $H_2O_2$ at 200° C. for 1 hour ("2.5 M H2O2 SLA").

Figure 7A:
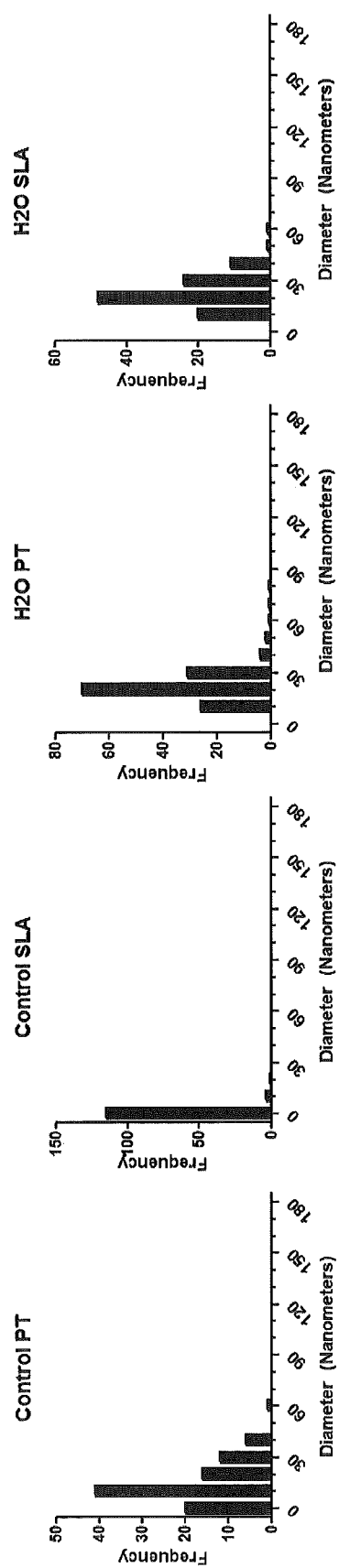
FIG. 7A provides histograms showing the distribution of the diameters of nanostructures on the surfaces of PT grade 2 titanium disks ("Control PT"), SLA grade 2 titanium disks ("Control SLA"), PT grade 2 titanium disks following exposure to a hydrothermal environment ($H_2O$ at 200° C. for 1 hour; "H2O PT") and SLA grade 2 titanium disks following exposure to a hydrothermal environment ($H_2O$ at 200° C. for 1 hour; "H2O SLA").
Figure 7B:
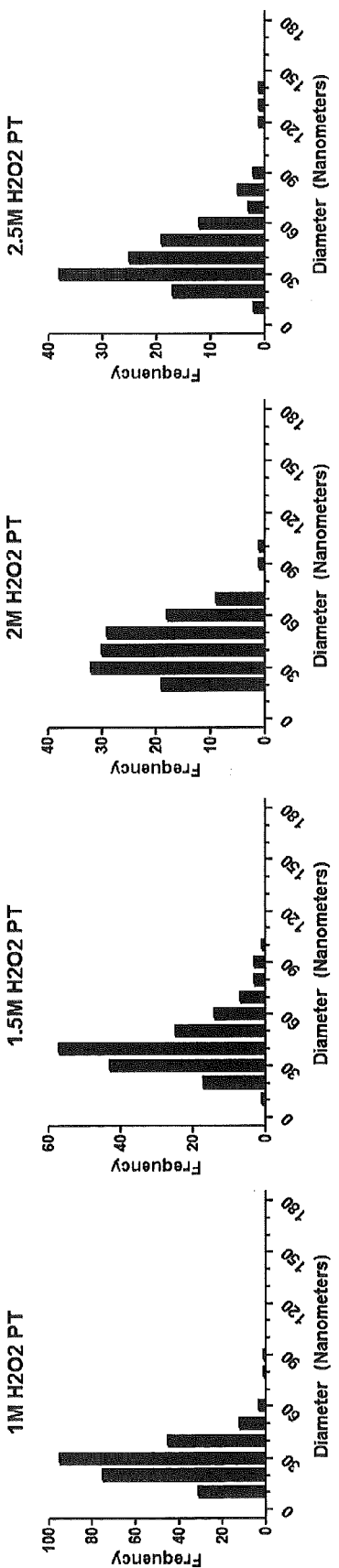
FIG. 7B provides histograms showing the distribution of the diameters of nanostructures on the surfaces of PT grade 2 titanium disks following exposure to different oxidative hydrothermal environments: 1 M $H_2O_2$ at 200° C. for 1 hour ("1 M H2O2 PT"); 1.5M $H_2O_2$ at 200° C. for 1 hour ("1.5 M H2O2 PT"); 2 M $H_2O_2$ at 200° C. for 1 hour ("2 M H2O2 PT"); and 2.5 M $H_2O_2$ at 200° C. for 1 hour ("2.5 M H2O2 PT").
Figure 7C:
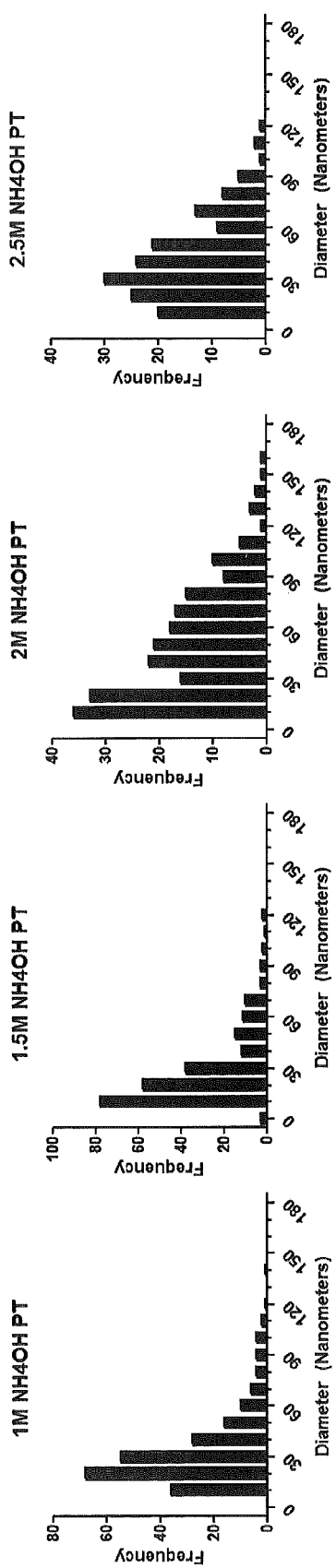
FIG. 7C provides histograms showing the distribution of the diameters of nanostructures on the surfaces of PT grade 2 titanium disks following exposure to different oxidative hydrothermal environments: 1 M $NH_4OH$ at 200° C. for 1 hour ("1 M NH4OH PT"); 1.5 M $NH_4OH$ at 200° C. for 1 hour ("1.5 M NH4OH PT"); 2 M $NH_4OH$ at 200° C. for 1 hour ("2 M NH4OH PT"); and 2.5 M $NH_4OH$ at 200° C. for 1 hour ("2.5 M NH4OH PT").
Figure 7D:
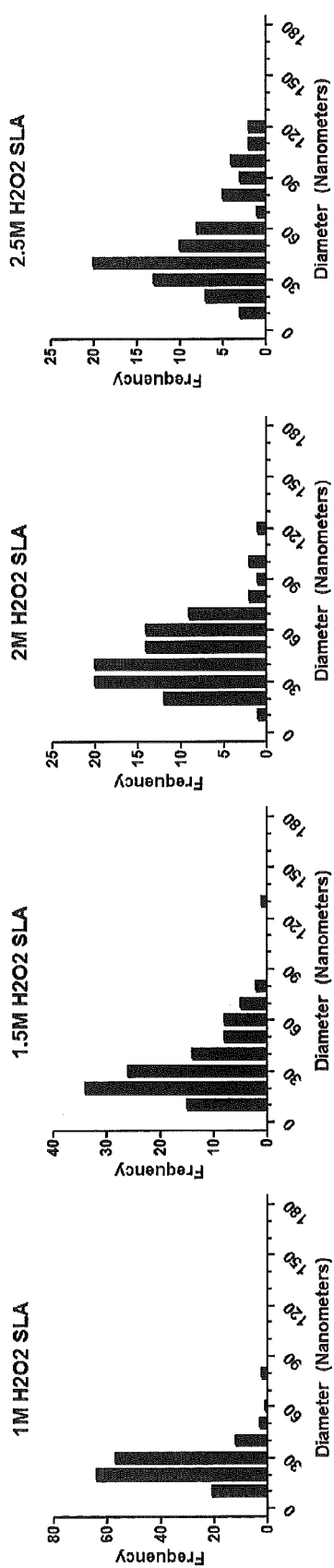
FIG. 7D provides histograms showing the distribution of the diameters of nanostructures on the surfaces of SLA grade 2 titanium disks following exposure to different oxidative hydrothermal environments: 1 M $H_2O_2$ at 200° C. for 1 hour ("1 M H2O2 SLA"); 1.5 M $H_2O_2$ at 200° C. for 1 hour ("1.5
Figure 7E:
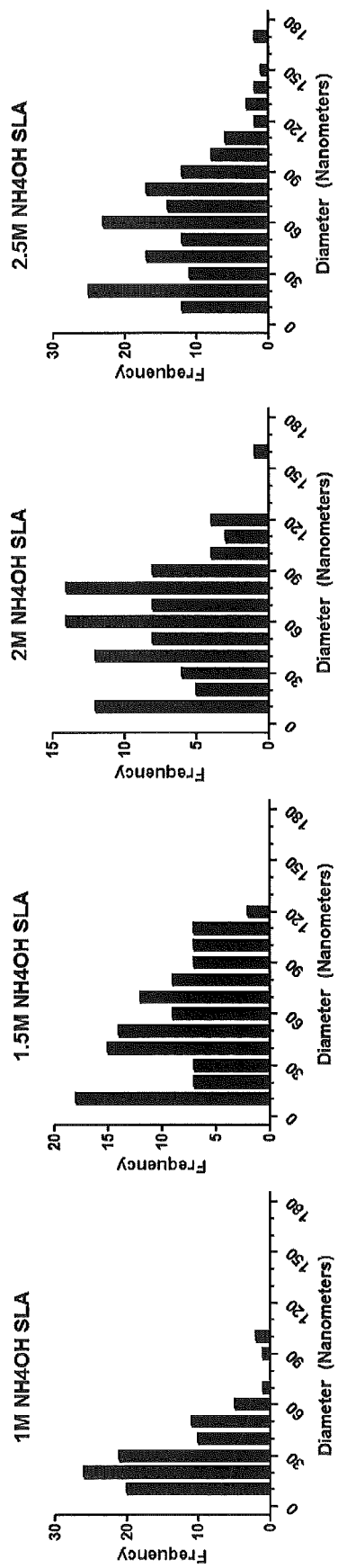

FIG. 7E provides histograms showing the distribution of the diameters of nanostructures on the surfaces of SLA grade 2 titanium disks following exposure to different oxidative hydrothermal environments: 1 M $NH_4OH$ at 200° C. for 1 hour ("1 M NH4OH SLA"); 1.5 M $NH_4OH$ at 200° C. for 1 hour ("1.5 M NH4OH SLA"); 2 M $NH_4OH$ at 200° C. for 1 hour ("2 M NH4OH SLA"); and 2.5 M $NH_4OH$ at 200° C. for 1 hour ("2.5 M NH4OH SLA").

Figure 8:
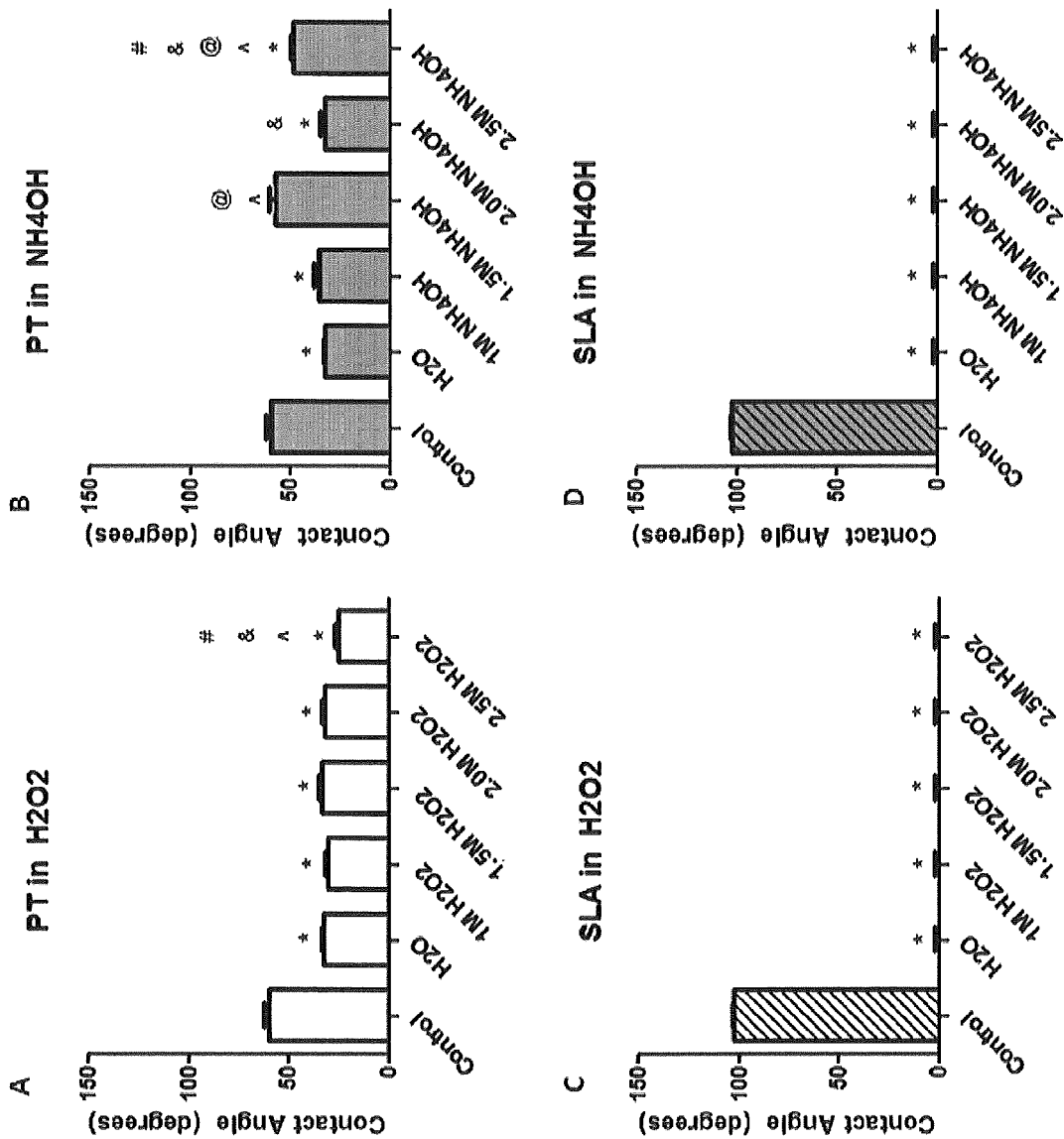

FIG. 8A is a graph showing the mean contact angle of the nanostructures on the surfaces of PT grade 2 titanium disks ("Control"), on the surfaces of PT grade 2 titanium disks following exposure to a hydrothermal environment ($H_2O$ at 200° C. for 1 hour; "H2O") and on the surfaces of PT grade 2 titanium disks following exposure to different oxidative hydrothermal environments: 1 M $H_2O_2$ at 200° C. for 1 hour ("1 M H2O2"); 1.5 M $H_2O_2$ at 200° C. for 1 hour ("1.5M H2O2"); 2 M $H_2O_2$ at 200° C. for 1 hour ("2.0M H2O2"); and 2.5 M $H_2O_2$ at 200° C. for 1 hour ("2.5M H2O2"). Standard error is shown for each column. *=statistical significance of p<0.05 versus control. ˆ=statistical significance of p<0.05 versus H20. @=statistical significance of p<0.05 versus 1 M H2O2. &=statistical significance of p<0.05 versus 1.5M H2O2. #=statistical significance of p<0.05 versus 2.0M H2O2.

FIG. 8B is a graph showing the mean contact angle of the nanostructures on the surfaces of PT grade 2 titanium disks ("Control"), on the surfaces of PT grade 2 titanium disks following exposure to a hydrothermal environment ($H_2O$ at 200° C. for 1 hour; "H2O") and on the surfaces of PT grade 2 titanium disks following exposure to different oxidative hydrothermal environments: 1 M $NH_4OH$ at 200° C. for 1 hour ("1 M NH4OH"); 1.5 M $NH_4OH$ at 200° C. for 1 hour ("1.5M NH4OH"); 2 M $NH_4OH$ at 200° C. for 1 hour ("2.0M NH4OH"); and 2.5 M $NH_4OH$ at 200° C. for 1 hour ("2.5M NH4OH"). Standard error is shown for each column. *=statistical significance of p<0.05 versus control. ˆ=statistical significance of p<0.05 versus H20. @=statistical significance of p<0.05 versus 1 M NH4OH. &=statistical significance of p<0.05 versus 1.5M NH4OH. #=statistical significance of p<0.05 versus 2.0M NH4OH.

FIG. 8C is a graph showing the mean contact angle of the nanostructures on the surfaces of SLA grade 2 titanium disks ("Control"), on the surfaces of SLA grade 2 titanium disks following exposure to a hydrothermal environment ($H_2O$ at 200° C. for 1 hour; "H2O") and on the surfaces of SLA grade 2 titanium disks following exposure to different oxidative hydrothermal environments: 1 M $H_2O_2$ at 200° C. for 1 hour ("1 M H2O2"); 1.5 M $H_2O_2$ at 200° C. for 1 hour ("1.5M H2O2"); 2 M $H_2O_2$ at 200° C. for 1 hour ("2.0M H2O2"); and 2.5 M $H_2O_2$ at 200° C. for 1 hour ("2.5M H2O2"). Standard error is shown for each column. *=statistical significance of p<0.05 versus control.

FIG. 8D is a graph showing the mean contact angle of the nanostructures on the surfaces of SLA grade 2 titanium disks ("Control"), on the surfaces of SLA grade 2 titanium disks following exposure to a hydrothermal environment ($H_2O$ at 200° C. for 1 hour; "H2O") and on the surfaces of SLA grade 2 titanium disks following exposure to different oxidative hydrothermal environments: 1 M $NH_4OH$ at 200° C. for 1 hour ("1 M NH4OH"); 1.5 M $NH_4OH$ at 200° C. for 1 hour ("1.5M NH4OH"); 2 M $NH_4OH$ at 200° C. for 1 hour ("2.0M NH4OH"); and 2.5 M $NH_4OH$ at 200° C. for 1 hour ("2.5M NH4OH"). Standard error is shown for each column. *=statistical significance of p<0.05 versus control.

Figure 9:
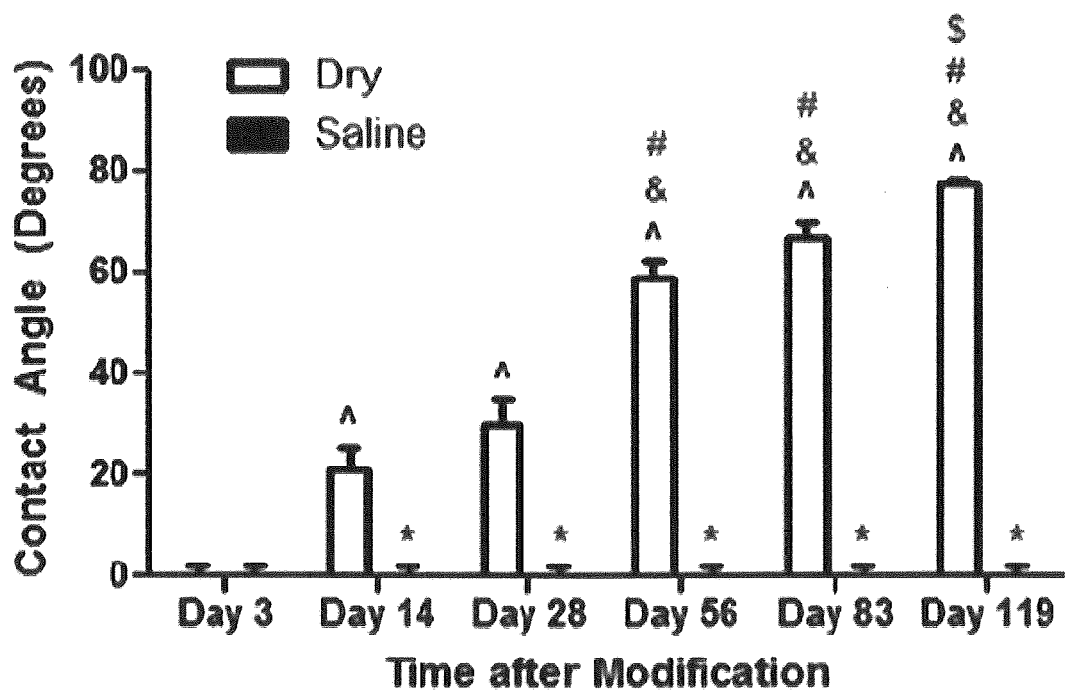
Figure 9:
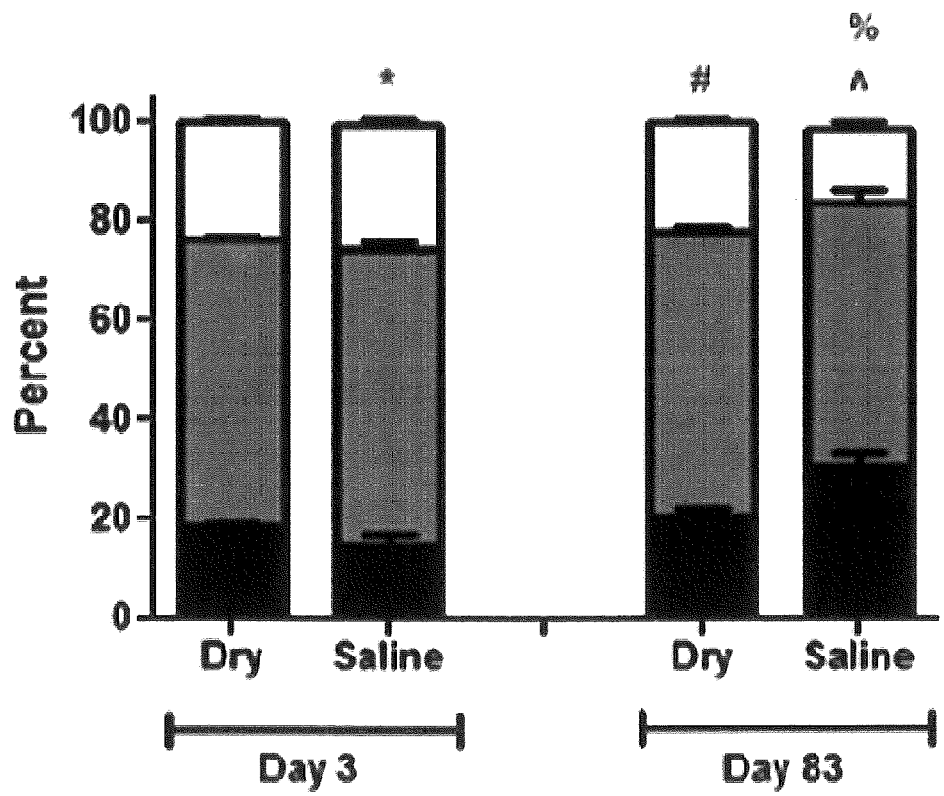

FIG. 9A is a graph showing the mean contact angle of nanostructures on the surfaces of SLA grade 2 titanium disks following exposure to a hydrothermal environment ($H_2O$ at 200° C. for 1 hour) and storage in air ("Dry") or saline solution ("Saline") for 3, 14, 28, 56, 83 or 119 days. Standard error is shown for each column. *=statistical significance of p<0.05 versus dry storage for an equal number of days. ˆ=statistical significance of p<0.05 versus dry storage for 3 days. &=statistical significance of p<0.05 versus dry storage for 14 days. #=statistical significance of p<0.05 versus dry storage for 28 days. $=statistical significance of p<0.05 versus dry storage for 56 days.

FIG. 9B is a graph showing the mean surface composition of SLA grade 2 titanium disks following exposure to a hydrothermal environment ($H_2O$ at 200° C. for 1 hour) and storage in air ("Dry") or saline solution ("Saline") for 3 or 83 days. The white portion of each bar represents titanium. The gray portion of each bar represents oxygen. The black portion of each bar represents carbon. Standard error is shown for each column. *=statistical significance of p<0.05 versus dry storage for 3 days. #=statistical significance of p<0.05 versus dry storage for 3 days. ˆ=statistical significance of p<0.05 versus saline storage for 3 days. %=statistical significance of p<0.05 versus dry storage for 83 days.

Figure 10A:
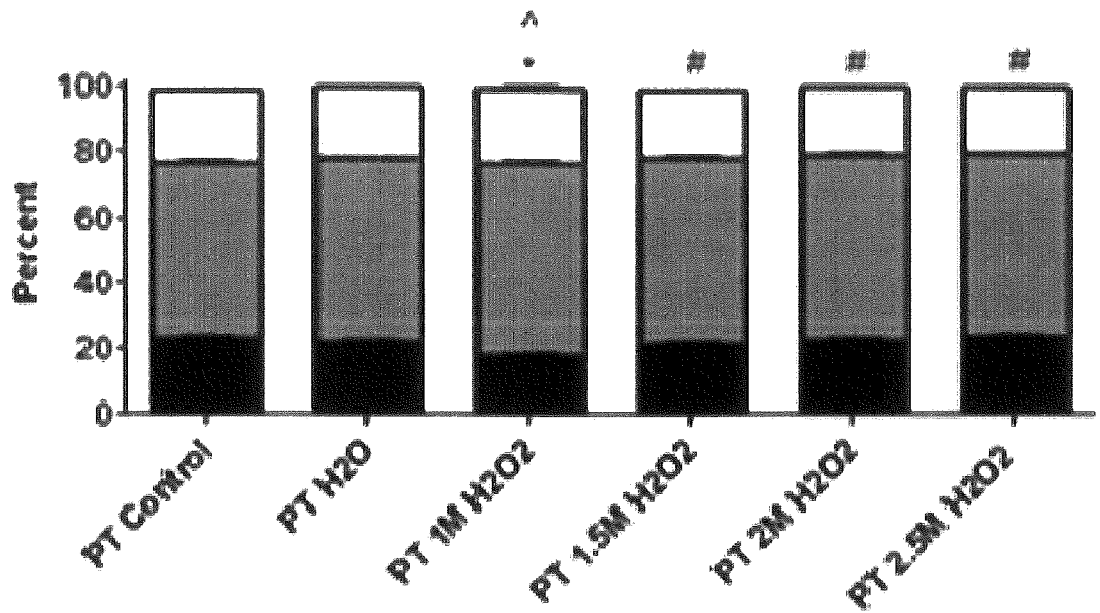

FIG. 10A is a graph showing the mean surface composition of PT grade 2 titanium disks ("PT Control"), PT grade 2 titanium disks following exposure to a hydrothermal environment ($H_2O$ at 200° C. for 1 hour; "PT H2O") and PT grade 2 titanium disks following exposure to different oxidative hydrothermal environments: 1 M $H_2O_2$ at 200° C. for 1 hour ("PT 1M H2O2"); 1.5 M $H_2O_2$ at 200° C. for 1 hour ("PT 1.5M H2O2"); 2 M $H_2O_2$ at 200° C. for 1 hour ("PT 2M H2O2"); and 2.5 M $H_2O_2$ at 200° C. for 1 hour ("PT 2.5M H2O2"). The white portion of each bar represents titanium. The gray portion of each bar represents oxygen. The black portion of each bar represents carbon. Standard error is shown for each column. *=statistical significance of p<0.05 versus PT Control. ˆ=statistical significance of p<0.05 versus PT H2O. #=statistical significance of p<0.05 versus PT 2M H2O2.

Figure 10B:
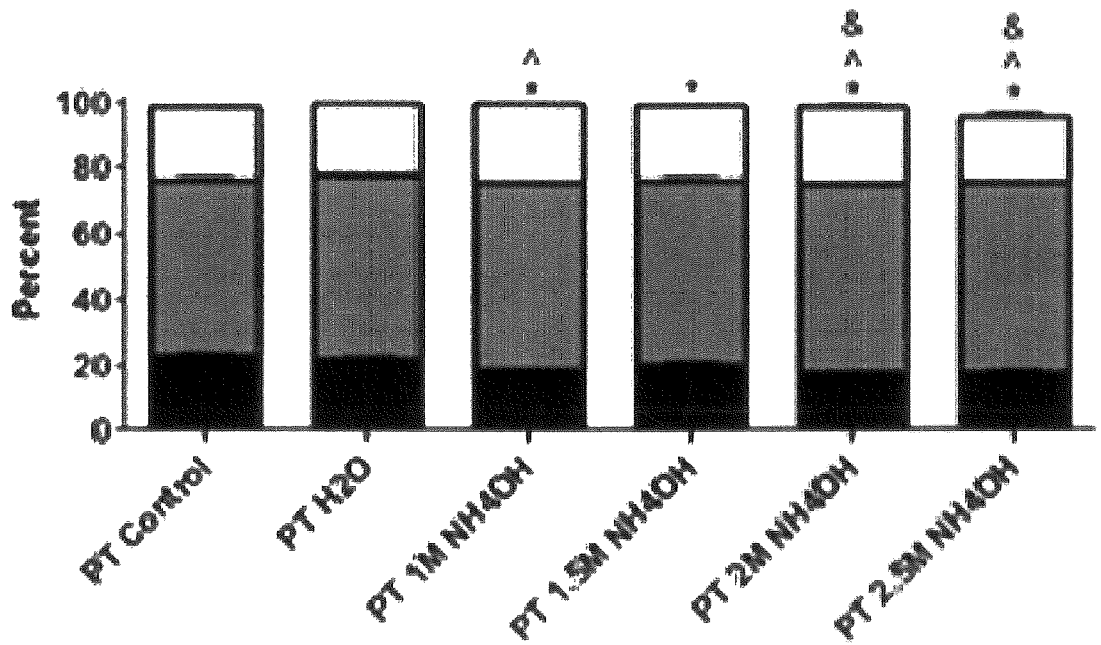

FIG. 10B is a graph showing the mean surface composition of PT grade 2 titanium disks ("PT Control"), PT grade 2 titanium disks following exposure to a hydrothermal environment ($H_2O$ at 200° C. for 1 hour; "PT H2O") and PT grade 2 titanium disks following exposure to different oxidative hydrothermal environments: 1 M $NH_4OH$ at 200° C. for 1 hour ("PT 1M NH4OH"); 1.5 M $NH_4OH$ at 200° C. for 1 hour ("PT 1.5M NH4OH"); 2 M $NH_4OH$ at 200° C. for 1 hour ("PT 2M NH4OH"); and 2.5 M $NH_4OH$ at 200° C. for 1 hour ("PT 2.5M NH4OH"). The white portion of each bar represents titanium. The gray portion of each bar represents oxygen. The black portion of each bar represents carbon. Standard error is shown for each column. *=statistical significance of p<0.05 versus PT Control. ˆ=statistical significance of p<0.05 versus PT H20. @=statistical significance of p<0.05 versus PT 1M NH4OH. &=statistical significance of p<0.05 versus PT 1.5M NH4OH.

Figure 10C:
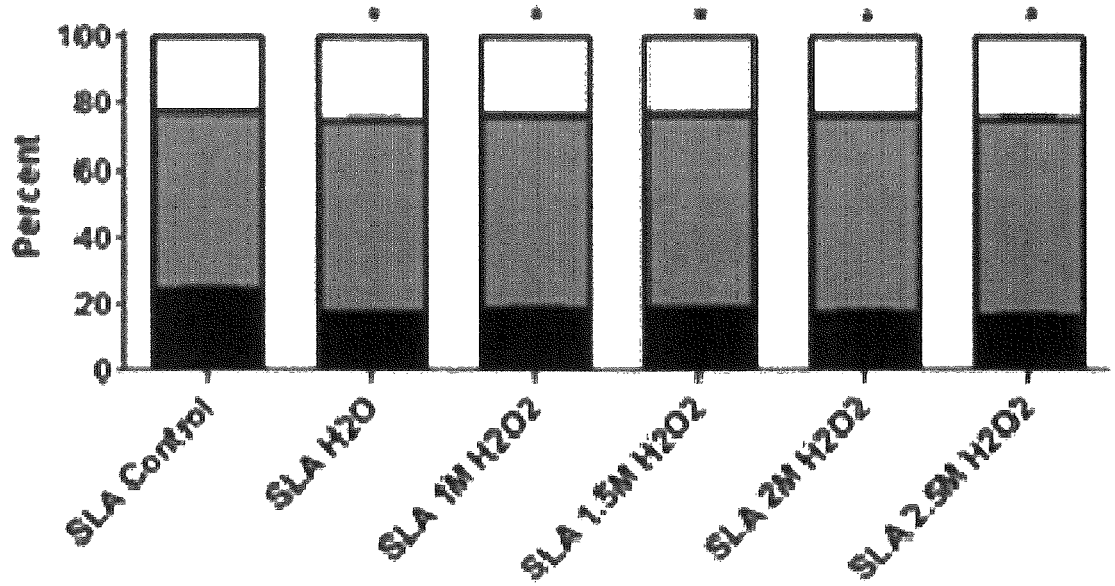

FIG. 10C is a graph showing the mean surface composition of SLA grade 2 titanium disks ("SLA Control"), SLA grade 2 titanium disks following exposure to a hydrothermal environment ($H_2O$ at 200° C. for 1 hour; "SLA H2O") and SLA grade 2 titanium disks following exposure to different oxidative hydrothermal environments: 1 M $H_2O_2$ at 200° C. for 1 hour ("SLA 1M H2O2"); 1.5 M $H_2O_2$ at 200° C. for 1 hour ("SLA 1.5M H2O2"); 2 M $H_2O_2$ at 200° C. for 1 hour ("SLA 2M H2O2"); and 2.5 M $H_2O_2$ at 200° C. for 1 hour ("SLA 2.5M H2O2"). The white portion of each bar represents titanium. The gray portion of each bar represents oxygen. The black portion of each bar represents carbon. Standard error is shown for each column. *=statistical significance of $p<0.05$ versus SLA Control.

Figure 10D:
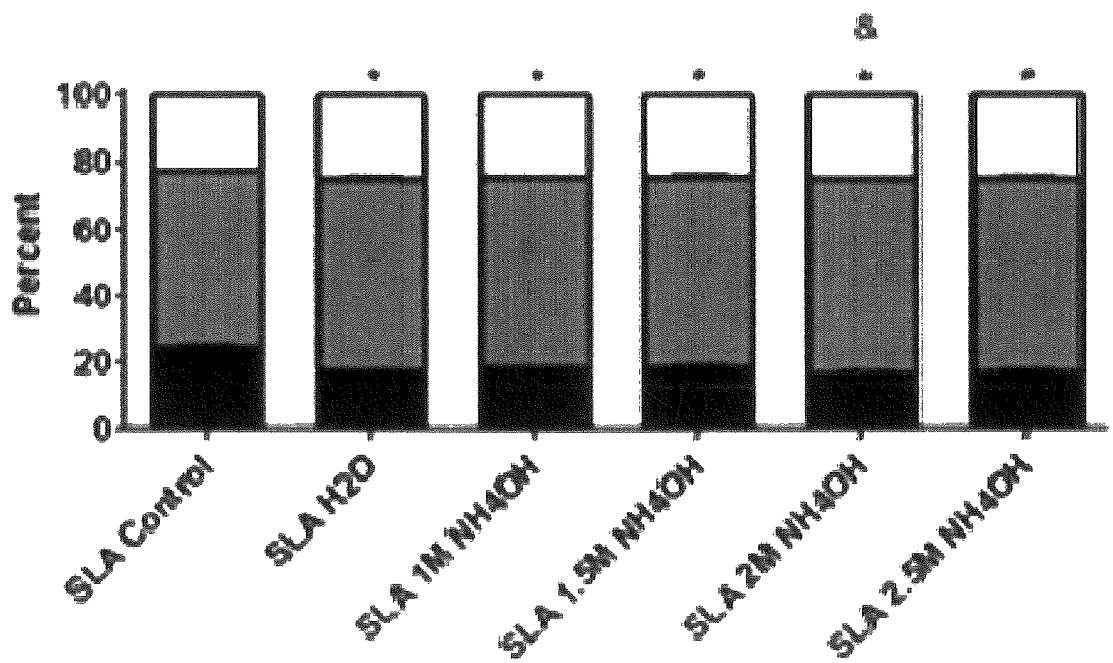

FIG. 10D is a graph showing the mean surface composition of SLA grade 2 titanium disks ("SLA Control"), SLA grade 2 titanium disks following exposure to a hydrothermal environment ($H_2O$ at 200° C. for 1 hour; "SLA H2O") and SLA grade 2 titanium disks following exposure to different oxidative hydrothermal environments: 1 M $NH_4OH$ at 200° C. for 1 hour ("SLA 1M NH4OH"); 1.5 M $NH_4OH$ at 200° C. for 1 hour ("SLA 1.5M NH4OH"); 2 M $NH_4OH$ at 200° C. for 1 hour ("SLA 2M NH4OH"); and 2.5 M $NH_4OH$ at 200° C. for 1 hour ("SLA 2.5M NH4OH"). The white portion of each bar represents titanium. The gray portion of each bar represents oxygen. The black portion of each bar represents carbon. Standard error is shown for each column. *=statistical significance of $p<0.05$ versus SLA Control. &=statistical significance of $p<0.05$ versus SLA 1.5M NH4OH.

Figure 11:
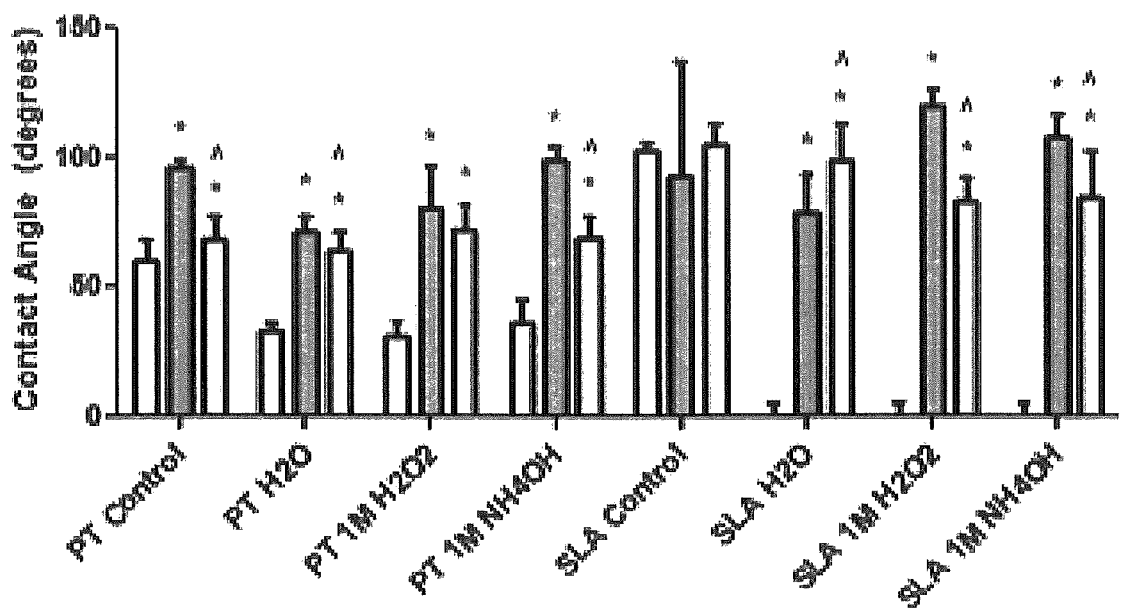
Figure 11:
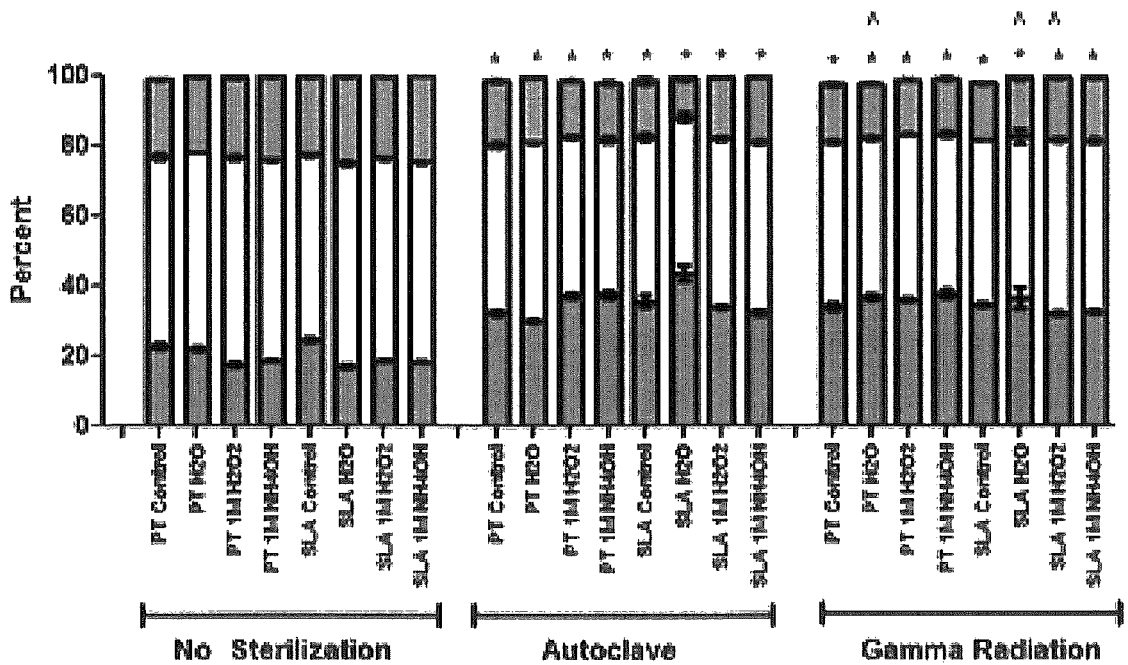

FIG. 11A is a graph showing the mean contact angle after ultrasonic cleaning with microsoap and ultrapure distilled water ("Clean"), ultrasonic cleaning with microsoap and ultrapure distilled water followed by autoclave sterilization at 121° C. for 30 minutes ("Autoclave") or ultrasonic cleaning with microsoap and ultrapure distilled water followed by gamma irradiation (25 kGy overnight; "Gamma") of nanostructures on the surfaces of PT grade 2 titanium disks ("PT Control"), on the surfaces of PT grade 2 titanium disks exposed to a hydrothermal environment ($H_2O$ at 200° C. for 1 hour; "PT H2O"), on the surfaces of PT grade 2 titanium disks exposed to an oxidative hydrothermal environment (1 M $H_2O_2$ at 200° C. for 1 hour; "PT 1M H2O2"), on the surfaces of PT grade 2 titanium disks exposed to a different oxidative hydrothermal environment (1 M $NH_4OH$ at 200° C. for 1 hour; "PT 1M NH4OH"), on the surfaces of SLA grade 2 titanium disks ("SLA Control"), on the surfaces of SLA grade 2 titanium disks exposed to a hydrothermal environment ($H_2O$ at 200° C. for 1 hour; "SLA H2O"), on the surfaces of SLA grade 2 titanium disks exposed to an oxidative hydrothermal environment (1 M $H_2O_2$ at 200° C. for 1 hour; "SLA 1M H2O2") and on the surfaces of SLA grade 2 titanium disks exposed to a different oxidative hydrothermal environment (1 M $NH_4OH$ at 200° C. for 1 hour; "SLA 1M NH4OH"). The white bars represent Clean. The dark gray bars represent Autoclave. The light gray bars represent Gamma. Standard error is shown for each column. *=statistical significance of $p<0.05$ versus corresponding Clean. ^=statistical significance of $p<0.05$ versus corresponding Autoclave.

FIG. 11B is a graph showing the mean surface composition after ultrasonic cleaning with microsoap and ultrapure distilled water ("No sterilization"), ultrasonic cleaning with microsoap and ultrapure distilled water followed by autoclave sterilization at 121° C. for 30 minutes ("Autoclave") or ultrasonic cleaning with microsoap and ultrapure distilled water followed by gamma irradiation (25 kGy overnight; "Gamma") of PT grade 2 titanium disks ("PT Control"), PT grade 2 titanium disks exposed to a hydrothermal environment ($H_2O$ at 200° C. for 1 hour; "PT H2O"), PT grade 2 titanium disks exposed to an oxidative hydrothermal environment (1 M $H_2O_2$ at 200° C. for 1 hour; "PT 1M H2O2"), PT grade 2 titanium disks exposed to a different oxidative hydrothermal environment (1 M $NH_4OH$ at 200° C. for 1 hour; "PT 1M NH4OH"), SLA grade 2 titanium disks ("SLA Control"), SLA grade 2 titanium disks exposed to a hydrothermal environment ($H_2O$ at 200° C. for 1 hour; "SLA H2O"), SLA grade 2 titanium disks exposed to an oxidative hydrothermal environment (1 M $H_2O_2$ at 200° C. for 1 hour; "SLA 1M H2O2") and SLA grade 2 titanium disks exposed to a different oxidative hydrothermal environment (1 M $NH_4OH$ at 200° C. for 1 hour; "SLA 1M NH4OH"). The top portion of each bar represents titanium. The middle portion of each bar represents oxygen. The bottom portion of each bar represents carbon. Standard error is shown for each column. Standard error is shown for each column. *=statistical significance of $p<0.05$ versus the amount of carbon in corresponding No Sterilization. ^=statistical significance of $p<0.05$ versus corresponding Autoclave.

Figure 12:
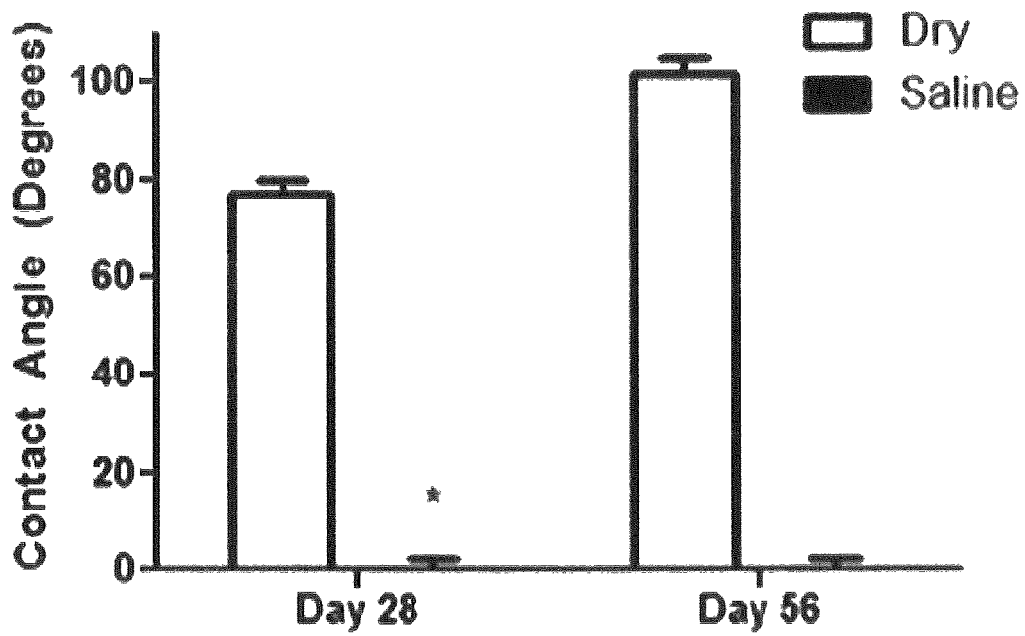
Figure 12:
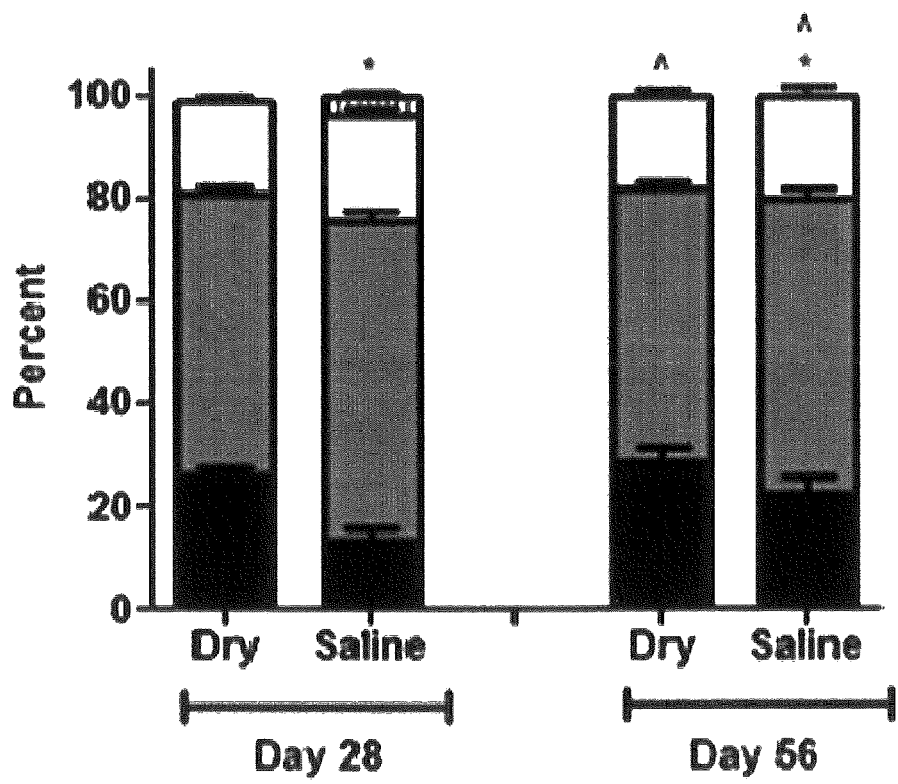

FIG. 12A is a graph showing the mean contact angle of nanostructures on the surfaces of SLA grade 2 titanium disks following exposure to a hydrothermal environment ($H_2O$ at 200° C. for 1 hour), ultrasonic cleaning with microsoap and ultrapure distilled water followed by gamma irradiation (25 kGy overnight) and then storage in air ("Dry") or saline solution ("Saline") for 28 or 56 days. Standard error is shown for each column. *=statistical significance of $p<0.05$ versus dry storage for the same number of days.

FIG. 12B is a graph showing the mean surface composition of SLA grade 2 titanium disks following exposure to a hydrothermal environment ($H_2O$ at 200° C. for 1 hour), ultrasonic cleaning with microsoap and ultrapure distilled water followed by gamma irradiation (25 kGy overnight) and then storage in air ("Dry") or saline solution ("Saline") for 28 or 56 days. The black portion of each bar represents carbon. The gray portion of each bar represents oxygen. The white portion of each bar represents titanium. The striped portion of the Day 28 Saline bar represents 3% silicon, which may have been the result of storing the samples in glass containers for gamma irradiation. Other trace contaminants found on the surface were less than 1%. Standard error is shown for each column. *=statistical significance of $p<0.05$ versus dry storage for the same number of days. ^=statistical significance of $p<0.05$ versus storage for 28 days in the corresponding storage medium (i.e., air or saline).

Figure 13:
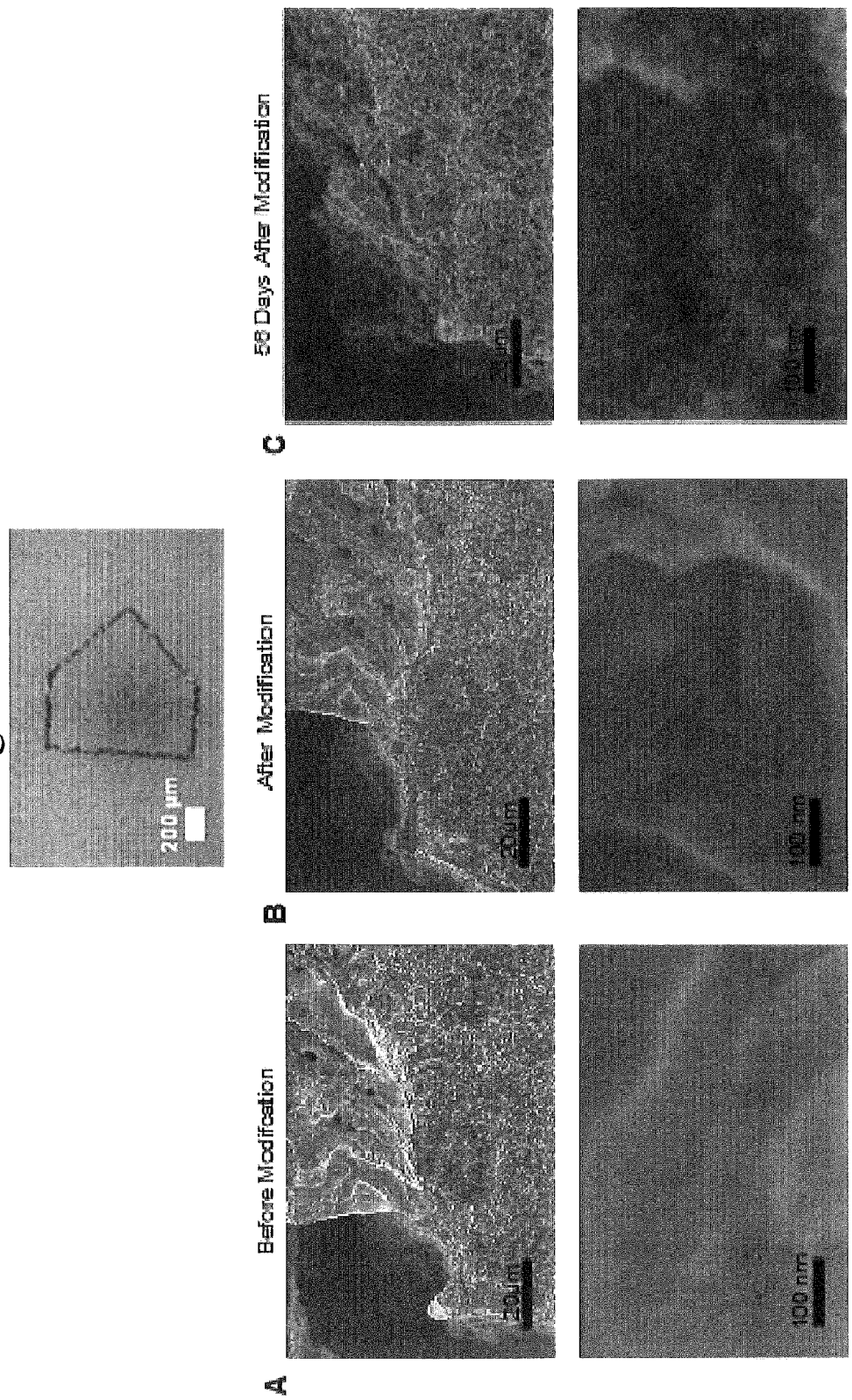

FIGS. 13A-13C provide SEM images of the surface of a SLA grade 2 titanium disk (A) immediately following laser etching, (B) following laser etching and exposure to a hydrothermal environment ($H_2O$ at 200° C. for 1 hour) and (C) following laser etching, exposure to a hydrothermal environment ($H_2O$ at 200° C. for 1 hour) and storage in saline solution for 56 days. The uppermost image shows the laser etching on the surface of the disk, which was used to ensure that the same location was imaged prior to hydrothermal modification, following hydrothermal modification and following storage in saline solution for 56 days. The upper row of images shows the surface of the disk at 1,000× magnification. The lower row of images shows the surface of the disk at 100,000× magnification.

Figure 14:
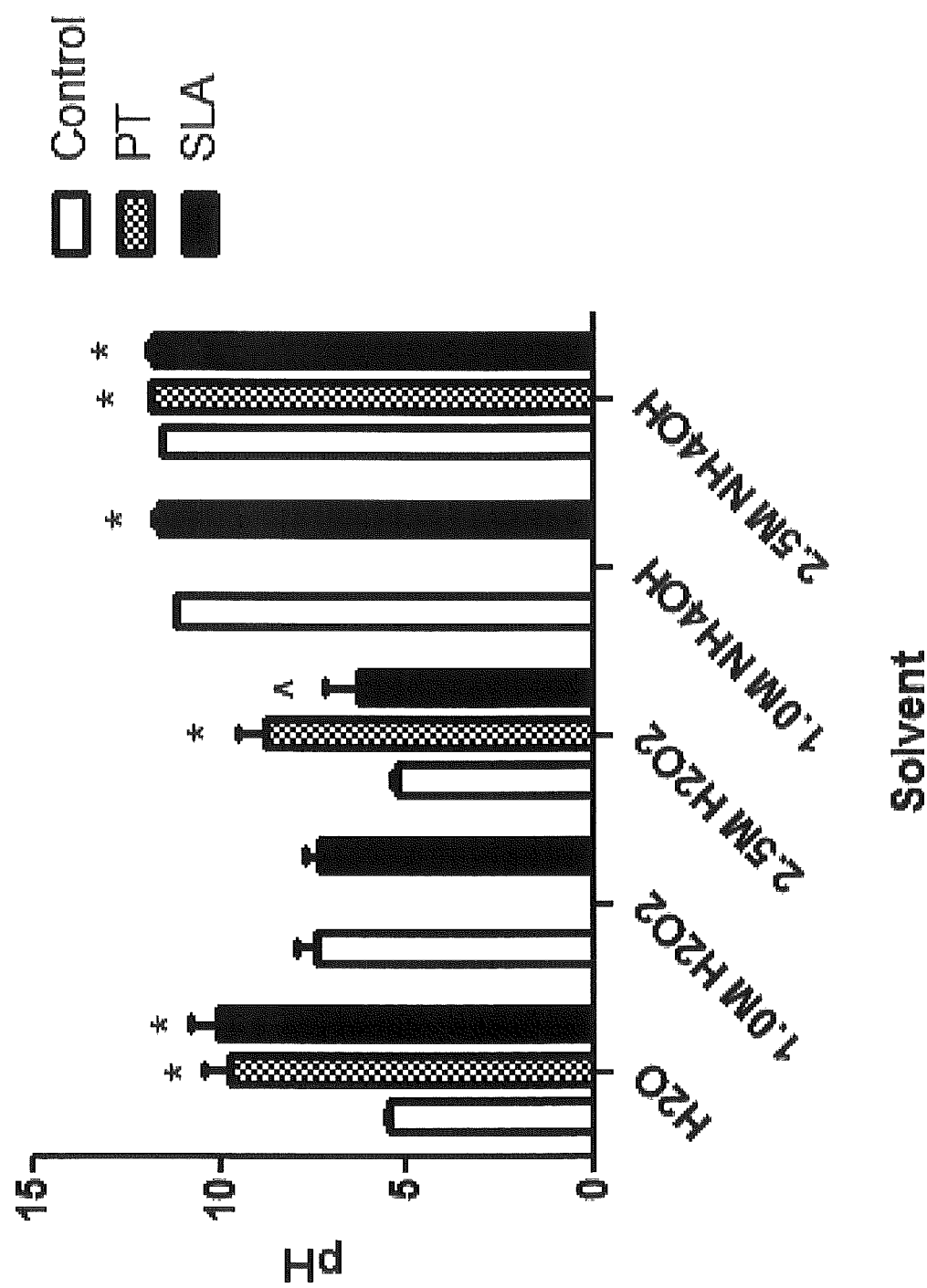

FIG. 14 is a graph showing the mean pH concentration of supernatant solutions before (white bars) and after exposure of PT grade 2 titanium disks (spotted bars) or SLA grade 2 titanium disks (black bars) to a hydrothermal environment ($H_2O$ at 200° C. for 1 hour; "H2O") or to different oxidative hydrothermal environments: 1 M $H_2O_2$ at 200° C. for 1 hour ("1.0M H2O2"), 2.5 M $H_2O_2$ at 200° C. for 1 hour ("2.5M H2O2"), 1 M $NH_4OH$ at 200° C. for 1 hour ("1.0M NH4OH") or 2.5 M $NH_4OH$ at 200° C. for 1 hour ("2.5M NH4OH"). Standard error is shown for each column. *=statistical significance of $p<0.05$ versus the corresponding Control.

Figure 15:
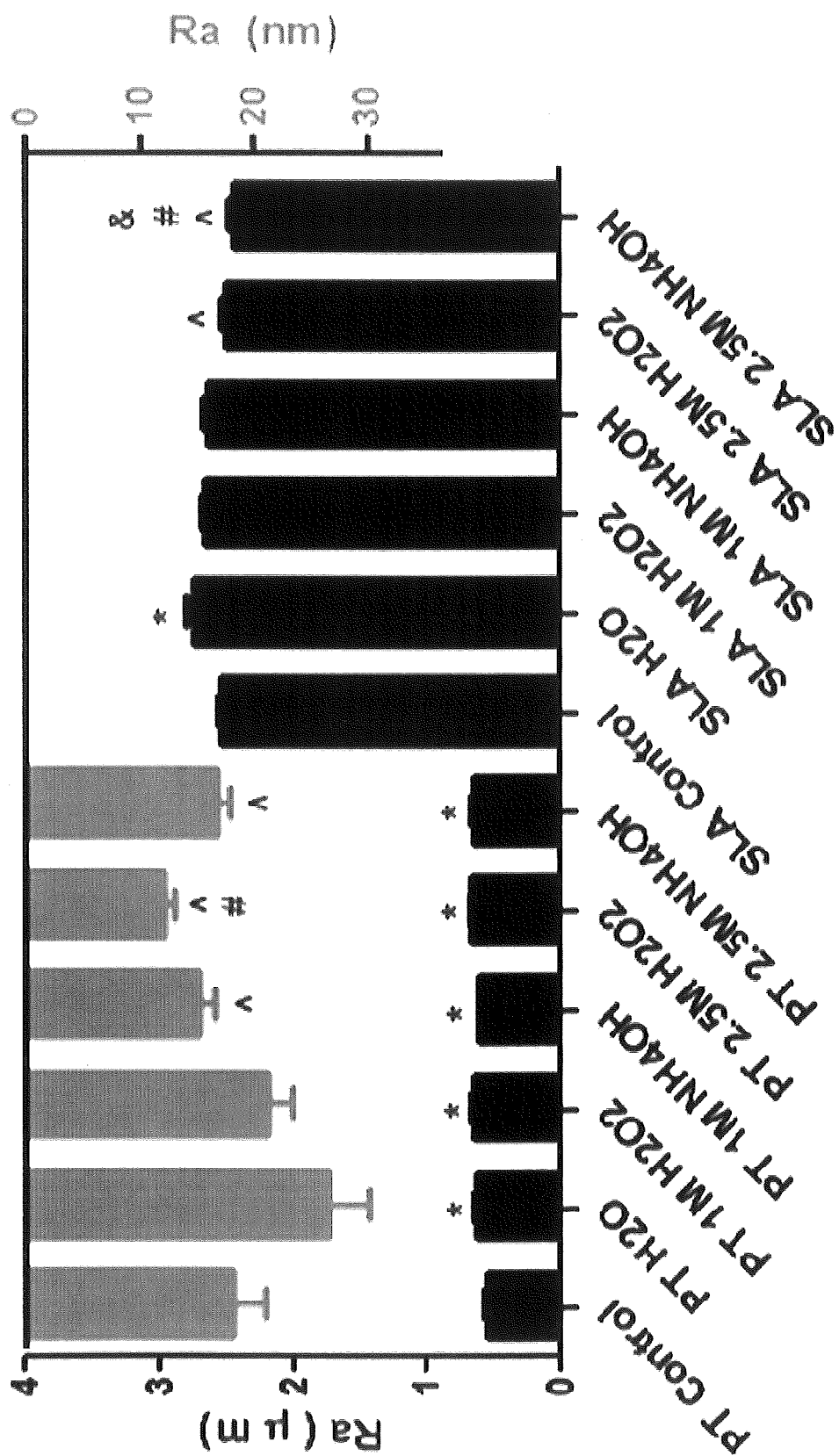

FIG. 15 is a graph showing the average surface roughness ($R_a$) of PT grade 2 titanium disks ("PT Control"); of PT grade 2 titanium disks exposed to a hydrothermal environment ($H_2O$ at 200° C. for 1 hour; "PT H2O"); of PT grade 2 titanium disks exposed to different oxidative hydrothermal environments: 1 M $H_2O_2$ at 200° C. for 1 hour ("PT 1M H2O2"), 1 M $NH_4OH$ at 200° C. for 1 hour ("PT 1M NH4OH"), 2.5 M $H_2O_2$ at 200° C. for 1 hour ("PT 2.5M H2O2") or 2.5 M $NH_4OH$ at 200° C. for 1 hour ("PT 2.5M NH4OH"); of SLA grade 2 titanium disks ("SLA Control"); of SLA grade 2 titanium disks exposed to a hydrothermal environment ($H_2O$ at 200° C. for 1 hour; "SLA H2O"); and of SLA grade 2 titanium disks exposed to different oxidative hydrothermal environments: 1 M $H_2O_2$ at 200° C. for 1 hour ("SLA 1M H2O2"), 1 M $NH_4OH$ at 200° C. for 1 hour ("SLA 1M NH4OH"), 2.5 M $H_2O_2$ at 200° C. for 1 hour ("SLA 2.5M H2O2") or 2.5 M $NH_4OH$ at 200° C. for 1 hour ("SLA 2.5M NH4OH"). Black bars represent the microscale surface roughness of the disks as measured by LCM. Gray bars represent the nanoscale surface roughness of the disks as measured by AFM. Standard error is shown for each column. *=statistical significance of $p<0.05$ versus the corresponding Control samples. ^=statistical significance of $p<0.05$ versus the corresponding H2O samples. #=statistical significance of $p<0.05$ versus the corresponding 1M H2O2 samples. &=statistical significance of $p<0.05$ versus the corresponding 1M NH4OH samples.

Figure 16:
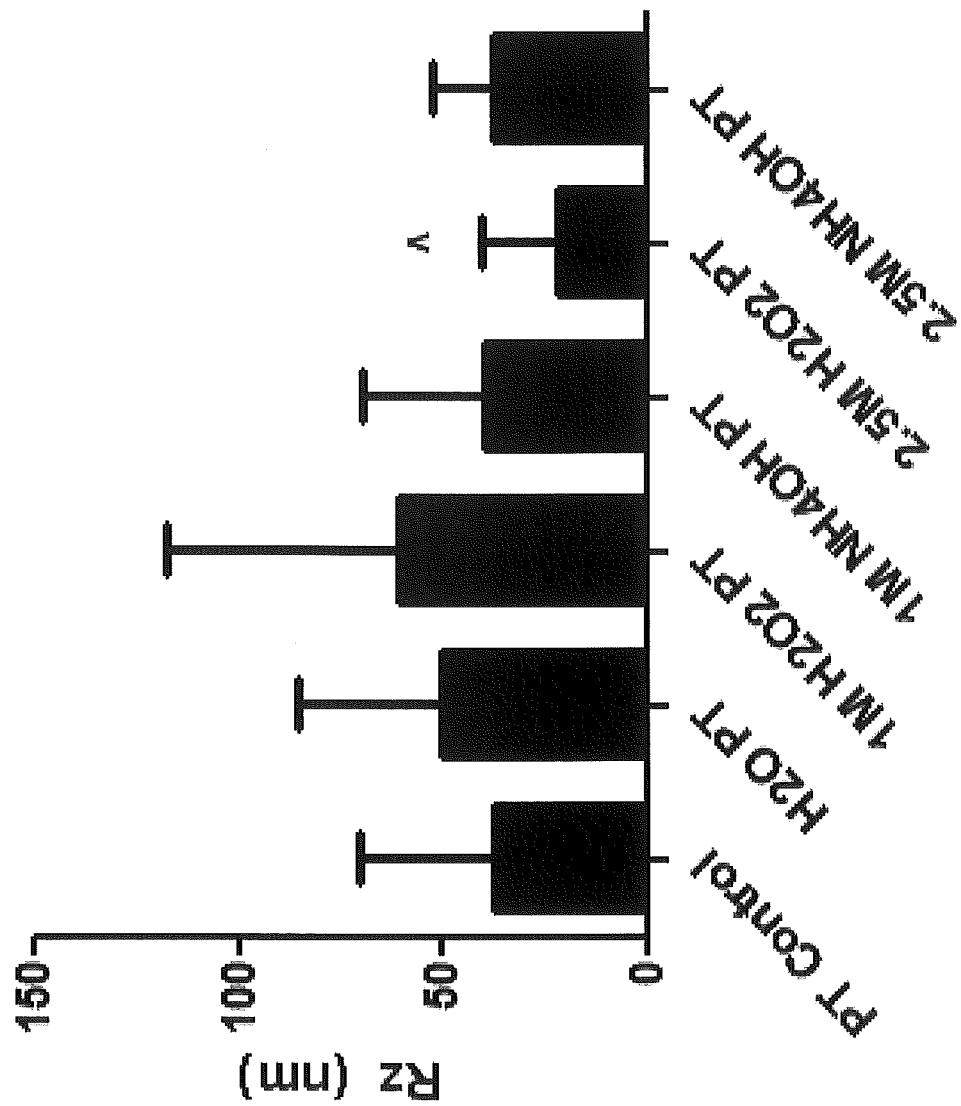

FIG. 16 is a graph showing the largest peak-valley differences of PT grade 2 titanium disks ("PT Control"), of PT grade 2 titanium disks exposed to a hydrothermal environment ($H_2O$ at 200° C. for 1 hour; "H2O PT") and of PT grade 2 titanium disks exposed to different oxidative hydrothermal environments: 1 M $H_2O_2$ at 200° C. for 1 hour ("1M H2O2 PT"), 1 M $NH_4OH$ at 200° C. for 1 hour ("1M NH4OH PT"), 2.5 M $H_2O_2$ at 200° C. for 1 hour ("2.5M H2O2 PT") or 2.5 M $NH_4OH$ at 200° C. for 1 hour ("2.5M NH4OH PT"). Standard error is shown for each column. ^=statistical significance of $p<0.05$ versus 1M H2O2 PT.

Figure 17:
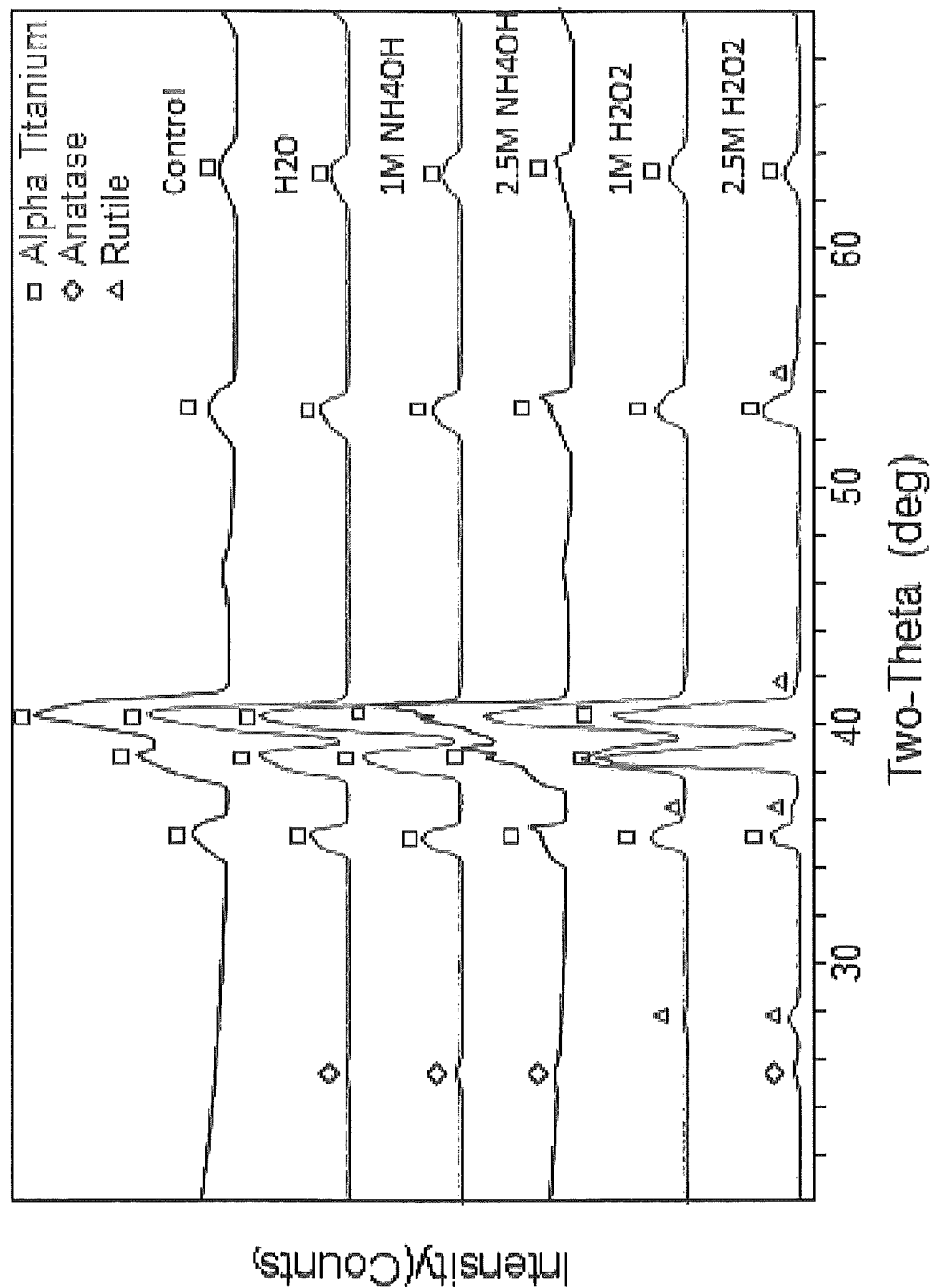

FIG. 17 shows x-ray diffraction spectra of a PT grade 2 titanium disk ("Control"), of a PT grade 2 titanium disk exposed to a hydrothermal environment ($H_2O$ at 200° C. for 1 hour; "H2O") and of PT grade 2 titanium disks exposed to different oxidative hydrothermal environments: 1 M $NH_4OH$ at 200° C. for 1 hour ("1M NH4OH"); 2.5 M $NH_4OH$ at 200° C. for 1 hour ("2.5M NH4OH"); 1 M $H_2O_2$ at 200° C. for 1 hour ("1M H2O2") and 2.5 M $H_2O_2$ at 200° C. for 1 hour ("2.5M H2O2").

DETAILED DESCRIPTION

The present invention is described more fully hereinafter with reference to particular embodiments of the present invention. This invention may, however, be embodied in many different forms and should not be construed as limited to the embodiments set forth herein. Rather, these embodiments are provided so that this disclosure will be thorough and complete, and will fully convey the scope of the present invention to those skilled in the art.

The terminology used herein is for the purpose of describing particular embodiments only, and is not intended to be limiting of the present invention.

It will be understood that when an element, such as a layer, region or substrate, is referred to as being "on," connected to" or "coupled to" another element, it can be directly on, connected or coupled to the other element, or one or more intervening elements may be present. In contrast, when an element is referred to as being "directly on," "directly connected to" or "directly coupled to" another element, there are no intervening elements present.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

Furthermore, relative terms, such as "lower" or "bottom" and "upper" or "top," may be used herein to describe one element's relationship to another element as illustrated in the figures. It will be understood that relative terms are intended to encompass different orientations of the device in addition to the orientation depicted in the figures. For example, if the device in the figures is turned over, elements described as being on the "lower" side of other elements would then be oriented on "upper" sides of the other elements. The exemplary term "lower", can therefore, encompasses both an orientation of "lower" and "upper," depending on the particular orientation of the figure.

Unless otherwise defined, all terms (including technical and scientific terms) used herein have the same meaning as commonly understood by one of ordinary skill in the art to which this invention belongs. Accordingly, these terms can include equivalent terms that are created after such time. It will be further understood that terms, such as those defined in commonly used dictionaries, should be interpreted as having a meaning that is consistent with their meaning in the present specification and in the context of the relevant art, and will not be interpreted in an idealized or overly formal sense unless expressly so defined herein.

As used herein, the singular forms "a", "an" and "the" are intended to include the plural forms as well, unless the context clearly indicates otherwise.

As used herein, the term "about," when used in reference to a measurable value such as an amount of time, a number of repetitions and the like, is meant to encompass both the specified amount and variations of 20%, 15%, 10%, 7.5%, 5%, 2.5% 1%, 0.5% or 0.1% of the specified amount.

As used herein, the term "and/or" refers to and encompasses any and all possible combinations of one or more of the associated listed items, as well as the lack of combinations when interpreted in the alternative ("or").

As used herein, the terms "comprise," "comprises," "comprising," "include," "includes," and "including" (and grammatical variants thereof) specify the presence of stated features, integers, steps, operations, elements, and/or components, but do not preclude the presence or addition of one or more other features, integers, steps, operations, elements, components, and/or groups thereof.

As used herein, the terms "implant" and "implant device" refer to any device that may be inserted into the body of a patient. In some embodiments, the implant comprises a cable, a nail, a pin, a plate, a screw, a stent and/or a wire.

As used herein, the term "nanostructure" refers to a structure having at least one dimension (e.g., diameter and/or height) that is about 1 nm to about 999 nm.

As used herein, the term "oxidative hydrothermal environment" refers to an environment comprising heat and water. In some embodiments, the temperature of the water is the range of about 5 to about 500° C. (e.g., about 25 to about 300° C., about 50 to about 250° C., about 100 to about 200° C., about 200° C.). In some embodiments, the oxidative hydrothermal environment also comprises at least one oxygen source other than water (e.g., gaseous oxygen). In some embodiments, the oxidative hydrothermal environment comprises one or more oxidizing agents (e.g., $Ca(OH)_2$, $CaO_2$, $H_2O_2$, NaOH, $NH_4OH$ and KOH).

As used herein, the term "patient" refers to both human subjects and animal subjects, including, but not limited to, mice, rats, rabbits, cats, dogs, pigs, horses, monkeys, apes, etc. The patient may be male or female. The patient may be of any suitable age, including infant, juvenile, adolescent, adult and geriatric ages. In some embodiments, the methods, devices and systems of the present invention may be used to repair and/or replace bone in a patient for medically diagnostic and/or therapeutic purposes. For example, the methods, devices and systems of the present invention may be used to treat mammalian subjects, such as mice, rats, pigs and monkeys, for medical research or veterinary purposes.

As used herein, the terms "pretreatment titanium disk" and "PT titanium disk" refer to a titanium disk that has been degreased in acetone and exposed to an aqueous solution consisting of 2% ammonium fluoride, 2% hydrofluoric acid and 10% nitric acid at 55° C. for 30 seconds. In some embodiments, the disk is formed from grade 2 titanium and is therefore referred to as a PT grade 2 titanium disk. In some embodiments, the disk is formed from grade 4 titanium and is therefore referred to as a PT grade 4 titanium disk.

As used herein, the terms "sand-blasted, large grit and acid etched grade 2 titanium disk" and "SLA titanium disk" refer to a PT titanium disk that has been sandblasted with corundum grit (0.25-0.50 μm) at 5 bar and then etching with a solution of hydrochloric and sulfuric acids heated above 100° C. for several minutes. In some embodiments, the disk is formed from grade 2 titanium and is therefore referred to as an SLA grade 2 titanium disk. In some embodiments, the disk is formed from grade 4 titanium and is therefore referred to as an SLA grade 4 titanium disk.

As used herein, the terms "treatment," "treat," and "treating" refer to reversing, alleviating, reducing the severity of, delaying the onset of, inhibiting the progress of or preventing a disease or disorder as described herein, or at least one symptom of a disease or disorder as described herein (e.g., treating one or more symptoms associated with a musculoskeletal disorder). In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved—for example, to prevent or delay their recurrence. Treatment may comprise introducing one or more implant devices of the present invention into the body of a patient. Treatment may be as an adjuvant treatment as further described herein.

Implant devices of the present invention may be used to treat a patient for any reason. In some embodiments, an implant device of the present invention is used to treat one or more disorders. Disorders for which treatment may be carried out include, but are not limited to, musculoskeletal disorders such as arthritis, back/neck pain, bone fractures and bone loss. In some embodiments, the implant device is used to replace one or more teeth (e.g., an unhealthy tooth or a missing tooth). In some embodiments, the implant device may be exposed to one or more live cells (e.g., stem cells) prior to being implanted in the patient. For example, an implant device of the present invention may be seeded with one or more love cells (e.g., mesenchymal stem cells) prior to implantation. Similarly, implant devices of the present invention may be exposed to one or more stem cells (e.g., mesenchymal stem cells) prior to implantation of the cells in a patient.

All publications, patent applications, patents, and other references mentioned herein are incorporated by reference in their entirety.

Aspects of the inventive concepts described with respect to one embodiment may be incorporated in a different embodiment although not specifically described relative thereto. That is, all embodiments and/or features of any embodiments can be combined in any way and/or combination. These and other objects and/or aspects of the present invention are explained in detail in the specification set forth below.

Methods

The present invention provides methods of manufacturing devices (e.g., implant devices) comprising nanoscale structures on at least one surface thereof. In some embodiments, the present invention provides a method of forming nanostructures on a surface of a device, said method comprising, consisting essentially of or consisting of exposing the surface of the device to an oxidative hydrothermal environment.

Methods of the present invention may be used to form nanostructures on the surface of any suitable device, including, but not limited to, biomedical and/or surgical implant devices, such as cables, wires, nails, pins, plates, prostheses, screws and stents. In some embodiments, methods of the present invention are used to form nanostructures on the surface of a dental implant (e.g., an endosteal, ramus frame, subperiosteal or intramucosal implant), an orthopedic implant (e.g., a hip, knee, elbow or shoulder implant, an ACL/PCL reconstructive implant, a mini-fragment implant, a small fragment implant or a large fragment implant), a craniomaxillofacial implant, spinal implant component/device (e.g., an articulating component), a prosthetic and transcutaneous device that requires direct skeletal attachment or a cardiovascular component/device (e.g., a stent). In some embodiments, methods of the present invention are used to form nanostructures on the surface of a device for which increased surface area and/or increased density of nanostructures may be advantageous, such as a catalytic converter.

Methods of the present invention may be used to form nanostructures on the surface of a device (e.g., an implant device) comprising any suitable material, including, but not limited to, metals, ceramics and/or polymers. In some embodiments, methods of the present invention are used to form nanostructures on the surface of a metallic implant device (i.e., an implant that consists essentially of or consists of one or more metals). In some embodiments, methods of the present invention are used to form nanostructures on the surface of a ceramic implant device i.e., an implant that consists essentially of or consists of one or more ceramics). In some embodiments, methods of the present invention are used to form nanostructures on the surface of an implant device comprising at least one metal portion and at least one ceramic portion. In some embodiments, methods of the present invention are used to form nanostructures on an implant device that consists essentially of or consists of metal and/or ceramic. In some embodiments of the invention, methods of the present invention are used to form nanostructures on an implant device that has a total metallic and/or ceramic content (i.e., metal content+ceramic content) greater than about 1%, 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99% or 99.5% by weight.

As noted above, methods of the present invention may be used to form nanostructures on the surface of a device (e.g., an implant device) comprising, consisting essentially of or consisting of one or more metals. Such metals may be present in the form of pure metals and/or metal alloys. The device may comprise, consist essentially of or consist of any suitable metal and/or metal alloy. Thus, in some embodiments, methods of the present invention are used to form nanostructures on the surface of a device comprising, consisting essentially of or consisting of one or more pure metals selected from the group consisting of magnesium, molybdenum, niobium, tantalum, titanium and zirconium and/or one or more metal alloys selected from the group consisting of cobalt alloys (e.g., cobalt-chromium-molybdenum alloys), iron alloys (e.g., iron-aluminum-manganese alloys, iron-aluminum-magnaese-carbon-chromium alloys and stainless steel), magnesium alloys (e.g., magnesium-aluminum alloys), nickel alloys (e.g., nickel-titanium alloys) and titanium alloys (e.g., $Ti_6Al_4V$, $Ti_6Al_4V_{0.5}Pt$, $Ti_6Al_7Nb$, $Ti_6Al_7Nb_{0.5}Pt$, $Ti_5Al_{1.5}B$, $Ti_5Al_{2.5}Fe$, $Ti_{4.2}Fe_{6.9}Cr$, $Ti_{4.2}Fe_{6.7}Cr_3Al$, $Ti_{15}Mo_5Zr_3al$, $Ti_{15}Mo_3Nb_3O$, $Ti_{12}Mo_6Zr_2Fe$, $Ti_{35}Nb_7Zr_5Nb$, $Ti_{35}Nb_7Zr_5Ta$, $Ti_{35}Nb_7Zr_5Ta_{0.4}O$, $Ti_{29}Nb_{13}Ta_{7.1}Zr$, $Ti_{29}Nb_{13}Ta_2Sn$, $Ti_{29}Nb_{13}Ta_{4.5}Zr$, $Ti_{29}Nb_{13}Ta_{4.6}Sn$, $Ti_{29}Nb_{13}Ta_6Sn$, $Ti_{29}Nb_{13}Ta_4Mo$, $Ti_{29}Nb_{13}Ta_{4.6}Zr$, $Ti_{16}Nb_{13}Ta_4Mo$, $Ti_{13}Nb_{13}Zr$, $Ti_{0.5}Pt$, titanium-molybdenum alloys and titanium-tantalum alloys).

As noted above, methods of the present invention may be used to form nanostructures on the surface of a device (e.g., an implant device) comprising one or more ceramics. The device may comprise, consist essentially of or consist of any suitable ceramic(s), including, but not limited to, titanium dioxide ($TiO_2$), zirconia ($ZrO_2$), alumina ($Al_2O_3$), barium titanate ($BaTiO_3$), calcium phosphate-based ceramics (e.g., hydroxyapatite) and lead-based piezoceramics (e.g., $Pb(Ti,Zr)O_3$).

Methods of the present invention may used to nanostructures symmetrical nanostructures and/or asymmetrical nanostructures. In some embodiments, the method is used to form at least one symmetrical nanostructure and at least one asymmetrical nanostructure. In some embodiments, at least about 50%, 55%, 60%, 65%, 70%, 75%, 80%, 85%, 90%, 95%, 96%, 97%, 98%, 99% or more of the nanostructures are symmetrical nanostructures. In some embodiments, at least about 50%, 55%, 60%, 65%, 70%, 75%, 80%, 85%, 90%, 95%, 96%, 97%, 98%, 99% or more of the nanostructures are asymmetrical nanostructures.

Methods of the present invention may be used to form nanostructures of any suitable dimensions. In some embodiments, the nanostructures have an average and/or mean diameter in the range of about 1 to about 200 nm (e.g., about 5 nm, about 10 nm, about 20 nm, about 30 nm, about 40 nm, about 50 nm, about 60 nm, about 70 nm, about 80 nm, about 90 nm, about 100 nm, about 125 nm, about 150 nm, about 200 nm). In some embodiments, the nanostructures have an average and/or mean diameter of at least about 1 to about 200 nm (at least about 5 nm, at least about 10 nm, at least about 20 nm, at least about 30 nm, at least about 40 nm, at least about 50 nm, at least about 60 nm, at least about 70 nm, at least about 80 nm, at least about 90 nm, at least about 100 nm, at least about 125 nm, at least about 150 nm, at least about 200 nm). In some embodiments, the nanostructures have an average and/or mean diameter of less than about 1 to about 200 nm (less than about 5 nm, less than about 10 nm, less than about 20 nm, less than about 30 nm, less than about 40 nm, less than about 50 nm, less than about 60 nm, less than about 70 nm, less than about 80 nm, less than about 90 nm, less than about 100 nm, less than about 125 nm, less than about 150 nm, less than about 200 nm). In some embodiments, the nanostructures have an average and/or mean height in the range of about 1 to about 300 nm (e.g., about 5 nm, about 10 nm, about 20 nm, about 30 nm, about 40 nm, about 50 nm, about 60 nm, about 70 nm, about 80 nm, about 90 nm, about 100 nm, about 125 nm, about 150 nm, about 200 nm, about 225 nm, about 250 nm, about 275 nm, about 300 nm). In some embodiments, the nanostructures have an average and/or mean height of at least about 1 to about 300 nm (at least about 5 nm, at least about 10 nm, at least about 20 nm, at least about 30 nm, at least about 40 nm, at least about 50 nm, at least about 60 nm, at least about 70 nm, at least about 80 nm, at least about 90 nm, at least about 100 nm, at least about 125 nm, at least about 150 nm, at least about 200 nm, at least about 225 nm, at least about 250 nm, at least about 275 nm, at least about 300 nm). In some embodiments, the nanostructures have an average and/or mean height of less than about 1 to about 300 nm (less than about 5 nm, less than about 10 nm, less than about 20 nm, less than about 30 nm, less than about 40 nm, less than about 50 nm, less than about 60 nm, less than about 70 nm, less than about 80 nm, less than about 90 nm, less than about 100 nm, less than about 125 nm, less than about 150 nm, less than about 200 nm, less than about 225 nm, less than about 250 nm, less than about 275 nm, less than about 300 nm). In some embodiments, the average and/or mean peak to valley height of the nanoscale structures is in the range of about 1 to about 400 nm (e.g., about 5 nm, about 10 nm, about 20 nm, about 30 nm, about 40 nm, about 50 nm, about 60 nm, about 70 nm, about 80 nm, about 90 nm, about 100 nm, about 125 nm, about 150 nm, about 200 nm, about 225 nm, about 250 nm, about 275 nm, about 300 nm, about 325 nm, about 350 nm, about 375 nm, about 400 nm). In some embodiments, the average and/or mean peak to valley height of the nanoscale structures is at least about 1 to about 300 nm (at least about 5 nm, at least about 10 nm, at least about 20 nm, at least about 30 nm, at least about 40 nm, at least about 50 nm, at least about 60 nm, at least about 70 nm, at least about 80 nm, at least about 90 nm, at least about 100 nm, at least about 125 nm, at least about 150 nm, at least about 200 nm, at least about 225 nm, at least about 250 nm, at least about 275 nm, at least about 300 nm, at least about 325 nm, at least about 350 nm, at least about 375 nm, at least about 400 nm). In some embodiments, the average and/or mean peak to valley height of the nanoscale structures is less than about 1 to about 300 nm (less than about 5 nm, less than about 10 nm, less than about 20 nm, less than about 30 nm, less than about 40 nm, less than about 50 nm, less than about 60 nm, less than about 70 nm, less than about 80 nm, less than about 90 nm, less than about 100 nm, less than about 125 nm, less than about 150 nm, less than about 200 nm, less than about 225 nm, less than about 250 nm, less than about 275 nm, less than about 300 nm, less than about 325 nm, less than about 350 nm, less than about 375 nm, less than about 400 nm).

Methods of the present invention may be used to form nanostructures in any suitable density. In some embodiments, the density of the nanostructures is in the range of about 5 to about 10,000 per square micrometer ("psm") (e.g., about 5 psm, about 25 psm, about 50 psm, about 75 psm, about 100 psm, about 150 psm, about 200 psm, about 250 psm, about 300 psm, about 350 psm, about 400 psm, about 450 psm, about 500 psm, about 600 psm, about 650 psm, about 700 psm, about 750 psm, about 800 psm, about 850 psm, about 900 psm, about 950 psm, about 1,000 psm, about 1,500 psm, about 2,000 psm, about 2,500 psm, about 3,000 psm, about 3,500 psm, about 4,000 psm, about 4,500 psm, about 5,000 psm, about 6,000 psm, about 7,000 psm, about 8,000 psm, about 9,000 psm, about 10,000 psm). In some embodiments, the density of the nanostructures is at least about 5 to about 10,000 per square micrometer ("psm") (e.g., at least about 5 psm, at least about 25 psm, at least about 50 psm, at least about 75 psm, at least about 100 psm, at least about 150 psm, at least about 200 psm, at least about 250 psm, at least about 300 psm, at least about 350 psm, at least about 400 psm, at least about 450 psm, at least about 500 psm, at least about 600 psm, at least about 650 psm, at least about 700 psm, at least about 750 psm, at least about 800 psm, at least about 850 psm, at least about 900 psm, at least about 950 psm, at least about 1,000 psm, at least about 1,500 psm, at least about 2,000 psm, at least about 2,500 psm, at least about 3,000 psm, at least about 3,500 psm, at least about 4,000 psm, at least about 4,500 psm, at least about 5,000 psm, at least about 6,000 psm, at least about 7,000 psm, at least about 8,000 psm, at least about 9,000 psm, at least about 10,000 psm). In some embodiments, the density of the nanostructures is less than about 5 to about 10,000 per square micrometer ("psm") (e.g., less than about 5 psm, less than about 25 psm, less than about 50 psm, less than about 75 psm, less than about 100 psm, less than about 150 psm, less than about 200 psm, less than about 250 psm, less than about 300 psm, less than about 350 psm, less than about 400 psm, less than about 450 psm, less than about 500 psm, less than about 600 psm, less than about 650 psm, less than about 700 psm, less than about 750 psm, less than about 800 psm, less than about 850 psm, less than about 900 psm, less than about 950 psm, less than about 1,000 psm, less than about 1,500 psm, less than about 2,000 psm, less than about 2,500 psm, less than about 3,000 psm, less than about 3,500 psm, less than about 4,000 psm, less than about 4,500 psm, less than about 5,000 psm, less than about 6,000 psm, less than about 7,000 psm, less than about 8,000 psm, less than about 9,000 psm, less than about 10,000 psm).

Devices may undergo any suitable pre-treatment prior to being exposed to the oxidative hydrothermal environment, including, but not limited to, degreasing, pickling, sand blasting, grit blasting, acid etching, laser etching and/or machining. For example, in some embodiments, an oxide is removed from the surface of the device prior to exposing the device to the oxidative hydrothermal environment. Likewise, the surface of the device may be cleaned prior to being exposed to the oxidative hydrothermal environment. In some embodiments, microscale features in the range of about 0.5 to about 500 μm may be formed on the surface of the device as a result of the pre-treatment(s) performed prior to exposing the surface to the oxidative hydrothermal environment. In some embodiments, the pre-treatments may give the surface of the device an average roughness ($S_a$) in the range of about 0.1 to about 5 μm.

Devices may be exposed to the oxidative hydrothermal environment for any suitable duration (e.g., a duration sufficient to generate one or more nanostructures on an exposed surface of the implant device). In some embodiments, the surface of the device is exposed to the oxidative hydrothermal environment for about 0.1 to about 4 hours (e.g., about 0.1 hour, about 0.2 hour, about 0.3 hour, about 0.4 hour, about 0.5 hour, about 0.75 hour, about 1 hour, about 1.25 hours, about 1.5 hours, about 1.75 hours, about 2 hours, about 2.25 hours, about 2.5 hours, about 2.75 hours, about 3 hours, about 3.25 hours, about 3.5 hours, about 3.75 hours, about 4 hours). In some embodiments, the surface of the device is exposed to the oxidative hydrothermal environment for at least about 0.1 to about 4 hours (e.g., at least about 0.1 hour, at least about 0.2 hour, at least about 0.3 hour, at least about 0.4 hour, at least about 0.5 hour, at least about 0.75 hour, at least about 1 hour, at least about 1.25 hours, at least about 1.5 hours, at least about 1.75 hours, at least about 2 hours, at least about 2.25 hours, at least about 2.5 hours, at least about 2.75 hours, at least about 3 hours, at least about 3.25 hours, at least about 3.5 hours, at least about 3.75 hours, at least about 4 hours). In some embodiments, the surface of the device is exposed to the oxidative hydrothermal environment for less than about 0.1 to about 4 hours (e.g., less than about 0.1 hour, less than about 0.2 hour, less than about 0.3 hour, less than about 0.4 hour, less than about 0.5 hour, less than about 0.75 hour, less than about 1 hour, less than about 1.25 hours, less than about 1.5 hours, less than about 1.75 hours, less than about 2 hours, less than about 2.25 hours, less than about 2.5 hours, less than about 2.75 hours, less than about 3 hours, less than about 3.25 hours, less than about 3.5 hours, less than about 3.75 hours, less than about 4 hours).

Devices may be exposed to any suitable oxidative hydrothermal environment. In some embodiments, the oxidative hydrothermal environment comprises an acidic oxidative solution (e.g., a solution comprising $CH_2O_2$, $C_2H_4O_2$, $C_4H_4O_4$, $C_2H_2O_4$, $H_2SO_4$ and/or $HNO_3$), a neutral- or near-neutral-pH oxidative solution (e.g., a solution comprising $H_2O$ and/or $H_2O_2$) and/or a caustic oxidative solution (e.g., a solution comprising $CaO_2$, $Ca(OH)_2$, KOH, NaOH, $NH_4OH$ and/or $(NH_4)_2S_2O_8$). In some such embodiments, the caustic solution has a concentration in the range of about 100 mM to about 10 M (e.g., about 0.25 M, about 0.5 M, about 0.75 M, about 1 M, about 1.5 M, about 2 M, about 2.5 M, about 3 M, about 4 M, about 5 M, about 6 M, about 7 M, about 8 M, about 9 M, about 10 M) and can generate one or more reactive species, such as $O_2$ and/or OH, at temperatures in the range of about 50 to about 400° C. In some embodiments, the oxidative hydrothermal environment comprises heat in the range of about 1 to about 400° C. (e.g., about 5° C., about 10° C., about 20° C., about 30° C., about 40° C., about 50° C., about 60° C., about 70° C., about 80° C., about 90° C., about 100° C., about 125° C., about 150° C., about 175° C., about 200° C., about 225° C., about 250° C., about 275° C., about 300° C., about 325° C., about 350° C., about 375° C., about 400° C.). In some embodiments, the oxidative hydrothermal environment comprises heat of at least about 1 to about 400° C. (e.g., at least about 5° C., at least about 10° C., at least about 20° C., at least about 30° C., at least about 40° C., at least about 50° C., at least about 60° C., at least about 70° C., at least about 80° C., at least about 90° C., at least about 100° C., at least about 125° C., at least about 150° C., at least about 175° C., at least about 200° C., at least about 225° C., at least about 250° C., about 275° C., about 300° C., about 325° C., about 350° C., about 375° C., about 400° C.). In some embodiments, the oxidative hydrothermal environment comprises heat of less than about 1 to about 400° C. (e.g., less than about 5° C., less than about 10° C., less than about 20° C., less than about 30° C., less than about 40° C., less than about 50° C., less than about 60° C., less than about 70° C., less than about 80° C., less than about 90° C., less than about 100° C., less than about 125° C., less than about 150° C., less than about 175° C., less than about 200° C., less than about 225° C., less than about 250° C., less than about 275° C., less than about 300° C., less than about 325° C., less than about 350° C., less than about 375° C., less than about 400° C.).

Exposing a surface of the device to an oxidative hydrothermal environment may comprise partially or completely submerging the surface in an oxidizing solution (e.g., a solution comprising $H_2O$, $H_2O_2$ and/or $NH_4OH$). Indeed, in some embodiments, the entire device is submerged in an oxidizing solution. The caustic solution may be heated to a target temperature before and/or during submergence of the surface of the device. In some embodiments, the temperature of the caustic solution is ramped up to a target temperature (e.g., about 200° C.) and then maintained at or around that target temperature for a duration sufficient to generate one or more nanostructures on the exposed surface of the implant device (e.g., about 1 hour).

Any suitable device or method may be used to generate heat for the oxidative hydrothermal environment, including, but not limited to, irradiation (e.g., microwave irradiation), steam heat (e.g., an autoclave sterilization device) and/or one or more heating element (e.g., a tube furnace). In some embodiments, exposing a surface of the device to an oxidative hydrothermal environment comprises heating an oxidizing solution with microwave radiation (e.g., microwave radiation having a frequency of about 2.45 GHz) in the range of about 50 to about 3,000 W (e.g., about 50 W, about 75 W, about 100 W, about 125 W, about 150 W, about 200 W, about 300 W, about 400 W, about 500 W, about 600 W, about 700 W, about 800 W, about 900 W, about 1000 W, about 1100 W, about 1200 W, about 1300 W, about 1400 W, about 1500 W, about 1600 W, about 1700 W, about 1800 W, about 1900 w, about 2000 W, about 2100 W, about 2200 W, about 2300 W, about 2400 W, about 2500 W, about 2600 W, about 2700 W, about 2800 W, about 2900 W, about 3000 W). In some embodiments, exposing a surface of the device to an oxidative hydrothermal environment comprises heating an oxidizing solution with microwave radiation (e.g., microwave radiation having a frequency of about 2.45 GHz) of at least about 50 to about 3,000 W (e.g., at least about 50 W, at least about 75 W, at least about 100 W, at least about 125 W, at least about 150 W, at least about 200 W, at least about 300 W, at least about 400 W, at least about 500 W, at least about 600 W, at least about 700 W, at least about 800 W, at least about 900 W, at least about 1000 W, at least about 1100 W, at least about 1200 W, at least about 1300 W, at least about 1400 W, at least about 1500 W, at least about 1600 W, at least about 1700 W, at least about 1800 W, at least about 1900 w, at least about 2000 W, at least about 2100 W, at least about 2200 W, at least about 2300 W, at least about 2400 W, at least about 2500 W, at least about 2600 W, at least about 2700 W, at least about 2800 W, at least about 2900 W, at least about 3000 W). In some embodiments, exposing a surface of the device to an oxidative hydrothermal environment comprises heating an oxidizing solution with microwave radiation (e.g., microwave radiation having a frequency of about 2.45 GHz) of less than about 50 to about 3,000 W (e.g., less than about 50 W, less than about 75 W, less than about 100 W, less than about 125 W, less than about 150 W, less than about 200 W, less than about 300 W, less than about 400 W, less than about 500 W, less than about 600 W, less than about 700 W, less than about 800 W, less than about 900 W, less than about 1000 W, less than about 1100 W, less than about 1200 W, less than about 1300 W, less than about 1400 W, less than about 1500 W, less than about 1600 W, less than about 1700 W, less than about 1800 W, less than about 1900 w, less than about 2000 W, less than about 2100 W, less than about 2200 W, less than about 2300 W, less than about 2400 W, less than about 2500 W, less than about 2600 W, less than about 2700 W, less than about 2800 W, less than about 2900 W, less than about 3000 W). Thus, in some embodiments, exposing a surface of the device to an oxidative hydrothermal environment comprises heating an oxidizing solution with microwave radiation having a frequency of about 2.45 GHz (e.g., about 800 W, about 1,600 W) until the caustic solution reaches a target temperature (e.g., about 200° C.) and/or using microwave irradiation (e.g., about 800 W, about 1,600 W) to maintain the temperature of an oxidizing solution at or around a target temperature (e.g., about 200° C.) for a duration sufficient to generate one or more nanostructures on the exposed surface of the device (e.g., about 1 hour).

Devices

The present invention provides devices comprising nanoscale structures on the surface thereof. In some embodiments, the device is an implant device.

In some embodiments, devices of the present invention comprise one or more nanostructures formed by a method of the present invention.

Devices of the present invention may be of any suitable type, including, but not limited to, biomedical and/or surgical implants, such as cables, wires, nails, pins, plates, prostheses, screws and stents. In some embodiments, the device is a dental implant (e.g., an endosteal, ramus frame, subperiosteal or intramucosal implant), an orthopedic implant (e.g., a hip, knee, elbow or shoulder implant, an ACL/PCL reconstructive implant, a mini-fragment implant, a small fragment implant or a large fragment implant), a craniomaxillofacial implant, spinal implant component/device (e.g., an articulating component), a prosthetic and transcutaneous device that requires direct skeletal attachment or a cardiovascular component/device (e.g., a stent). In some embodiments, the device is a device for which increased surface area and/or increased density of nanostructures may be advantageous, such as a catalytic converter.

Devices of the present invention may comprise any suitable material, including, but not limited to, metals, ceramics and/or polymers. In some embodiments, the device is a metallic device (i.e., a device that consists essentially of or consists of one or more metals). In some embodiments, the device is a ceramic device (i.e., a device that consists essentially of or consists of one or more ceramics). In some embodiments, the device comprises at least one metal portion and at least one ceramic portion. In some embodiments, the device consists essentially of or consists of metal and/or ceramic. In some embodiments of the invention, the device has a total metallic and/or ceramic content (i.e., metal content+ceramic content) greater than about 1%, 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99% or 99.5% by weight.

As noted above, devices of the present invention may comprise, consist essentially of or consist of one or more metals. Such metals may be present in the form of pure metals and/or metal alloys. The device may comprise, consist essentially of or consist of any suitable metal and/or metal alloy. Thus, in some embodiments, methods of the present invention are used to form nanostructures on the surface of a device comprising, consisting essentially of or consisting of one or more pure metals selected from the group consisting of magnesium, molybdenum, niobium, tantalum, titanium and zirconium and/or one or more metal alloys selected from the group consisting of cobalt alloys (e.g., cobalt-chromium-molybdenum alloys), iron alloys (e.g., iron-aluminum-manganese alloys, iron-aluminum-manganese-carbon-chromium alloys and stainless steel), magnesium alloys (e.g., magnesium-aluminum alloys), nickel alloys (e.g., nickel-titanium alloys) and titanium alloys (e.g., $Ti_6Al_4V$, $Ti_6Al_4V_{0.5}Pt$, $Ti_6Al_7Nb$, $Ti_6Al_7Nb_{0.5}Pt$, $Ti_5Al_{1.5}B$, $Ti_5Al_{2.5}Fe$, $Ti_{4.2}Fe_{6.9}Cr$, $Ti_{4.2}Fe_{6.7}Cr_3Al$, $Ti_{15}Mo_5Zr_3al$, $Ti_{15}Mo_3Nb_3O$, $Ti_{12}Mo_6Zr_2Fe$, $Ti_{35}Nb_7Zr_5Nb$, $Ti_{35}Nb_7Zr_5Ta$, $Ti_{35}Nb_7Zr_5Ta_{0.4}O$, $Ti_{29}Nb_{13}Ta_{7.1}Zr$, $Ti_{29}Nb_{13}Ta_2Sn$, $Ti_{29}Nb_{13}Ta_{4.5}Zr$, $Ti_{29}Nb_{13}Ta_{4.6}Sn$, $Ti_{29}Nb_{13}Ta_6Sn$, $Ti_{29}Nb_{13}Ta_4Mo$, $Ti_{29}Nb_{13}Ta_{4.6}Zr$, $Ti_{16}Nb_{13}Ta_4Mo$, $Ti_3Nb_{13}Zr$, $Ti_{0.5}Pt$, titanium-molybdenum alloys and titanium-tantalum alloys).

As noted above, devices of the present invention may comprise, consist essentially of or consist of one or more ceramics. The device may comprise, consist essentially of or consist of any suitable ceramic(s), including, but not limited to, titanium dioxide ($TiO_2$), zirconia ($ZrO_2$), alumina ($Al_2O_3$), barium titanate ($BaTiO_3$), calcium phosphate-based ceramics (e.g., hydroxyapatite) and lead-based piezoceramics (e.g., $Pb(Ti,Zr)O_3$).

Devices of the present invention may comprise any suitable type of nanostructures, including, but not limited to, symmetrical nanostructures and asymmetrical nanostructures. In some embodiments, the device comprises at least one symmetrical nanostructure and at least one asymmetrical nanostructure. In some embodiments, at least about 50%, 55%, 60%, 65%, 70%, 75%, 80%, 85%, 90%, 95%, 96%, 97%, 98%, 99% or more of the nanostructures are symmetrical nanostructures. In some embodiments, at least about 50%, 55%, 60%, 65%, 70%, 75%, 80%, 85%, 90%, 95%, 96%, 97%, 98%, 99% or more of the nanostructures are asymmetrical nanostructures.

Devices of the present invention may comprise nanostructures of any suitable dimensions. In some embodiments, the nanostructures have an average and/or mean diameter in the range of about 1 to about 200 nm (e.g., about 5 nm, about 10 nm, about 20 nm, about 30 nm, about 40 nm, about 50 nm, about 60 nm, about 70 nm, about 80 nm, about 90 nm, about 100 nm, about 125 nm, about 150 nm, about 200 nm). In some embodiments, the nanostructures have an average and/or mean diameter of at least about 1 to about 200 nm (at least about 5 nm, at least about 10 nm, at least about 20 nm, at least about 30 nm, at least about 40 nm, at least about 50 nm, at least about 60 nm, at least about 70 nm, at least about 80 nm, at least about 90 nm, at least about 100 nm, at least about 125 nm, at least about 150 nm, at least about 200 nm). In some embodiments, the nanostructures have an average and/or mean diameter of less than about 1 to about 200 nm (less than about 5 nm, less than about 10 nm, less than about 20 nm, less than about 30 nm, less than about 40 nm, less than about 50 nm, less than about 60 nm, less than about 70 nm, less than about 80 nm, less than about 90 nm, less than about 100 nm, less than about 125 nm, less than about 150 nm, less than about 200 nm). In some embodiments, the nanostructures have an average and/or mean height in the range of about 1 to about 300 nm (e.g., about 5 nm, about 10 nm, about 20 nm, about 30 nm, about 40 nm, about 50 nm, about 60 nm, about 70 nm, about 80 nm, about 90 nm, about 100 nm, about 125 nm, about 150 nm, about 200 nm, about 225 nm, about 250 nm, about 275 nm, about 300 nm). In some embodiments, the nanostructures have an average and/or mean height of at least about 1 to about 300 nm (at least about 5 nm, at least about 10 nm, at least about 20 nm, at least about 30 nm, at least about 40 nm, at least about 50 nm, at least about 60 nm, at least about 70 nm, at least about 80 nm, at least about 90 nm, at least about 100 nm, at least about 125 nm, at least about 150 nm, at least about 200 nm, at least about 225 nm, at least about 250 nm, at least about 275 nm, at least about 300 nm). In some embodiments, the nanostructures have an average and/or mean height of less than about 1 to about 300 nm (less than about 5 nm, less than about 10 nm, less than about 20 nm, less than about 30 nm, less than about 40 nm, less than about 50 nm, less than about 60 nm, less than about 70 nm, less than about 80 nm, less than about 90 nm, less than about 100 nm, less than about 125 urn, less than about 150 nm, less than about 200 nm, less than about 225 nm, less than about 250 nm, less than about 275 nm, less than about 300 nm). In some embodiments, the average and/or mean peak to valley height of the nanoscale structures is in the range of about 1 to about 400 nm (e.g., about 5 nm, about 10 nm, about 20 nm, about 30 nm, about 40 nm, about 50 nm, about 60 nm, about 70 nm, about 80 nm, about 90 nm, about 100 nm, about 125 nm, about 150 nm, about 200 nm, about 225 nm, about 250 nm, about 275 nm, about 300 nm, about 325 nm, about 350 nm, about 375 nm, about 400 nm). In some embodiments, the average and/or mean peak to valley height of the nanoscale structures is at least about 1 to about 300 nm (at least about 5 nm, at least about 10 nm, at least about 20 nm, at least about 30 nm, at least about 40 nm, at least about 50 nm, at least about 60 nm, at least about 70 nm, at least about 80 nm, at least about 90 nm, at least about 100 nm, at least about 125 nm, at least about 150 nm, at least about 200 nm, at least about 225 nm, at least about 250 nm, at least about 275 nm, at least about 300 nm, at least about 325 nm, at least about 350 mm, at least about 375 nm, at least about 400 nm). In some embodiments, the average and/or mean peak to valley height of the nanoscale structures is less than about 1 to about 300 nm (less than about 5 nm, less than about 10 nm, less than about 20 nm, less than about 30 nm, less than about 40 nm, less than about 50 nm, less than about 60 nm, less than about 70 nm, less than about 80 nm, less than about 90 nm, less than about 100 nm, less than about 125 nm, less than about 150 nm, less than about 200 nm, less than about 225 nm, less than about 250 nm, less than about 275 nm, less than about 300 nm, less than about 325 nm, less than about 350 nm, less than about 375 nm, less than about 400 nm).

Devices of the present invention may comprise nanostructures in any suitable density. In some embodiments, the density of the nanostructures is in the range of about 5 to about 10,000 per square micrometer ("psm") (e.g., about 5 psm, about 25 psm, about 50 psm, about 75 psm, about 100 psm, about 150 psm, about 200 psm, about 250 psm, about 300 psm, about 350 psm, about 400 psm, about 450 psm, about 500 psm, about 600 psm, about 650 psm, about 700 psm, about 750 psm, about 800 psm, about 850 psm, about 900 psm, about 950 psm, about 1,000 psm, about 1,500 psm, about 2,000 psm, about 2,500 psm, about 3,000 psm, about 3,500 psm, about 4,000 psm, about 4,500 psm, about 5,000 psm, about 6,000 psm, about 7,000 psm, about 8,000 psm, about 9,000 psm, about 10,000 psm). In some embodiments, the density of the nanostructures is at least about 5 to about 10,000 per square micrometer ("psm") (e.g., at least about 5 psm, at least about 25 psm, at least about 50 psm, at least about 75 psm, at least about 100 psm, at least about 150 psm, at least about 200 psm, at least about 250 psm, at least about 300 psm, at least about 350 psm, at least about 400 psm, at least about 450 psm, at least about 500 psm, at least about 600 psm, at least about 650 psm, at least about 700 psm, at least about 750 psm, at least about 800 psm, at least about 850 psm, at least about 900 psm, at least about 950 psm, at least about 1,000 psm, at least about 1,500 psm, at least about 2,000 psm, at least about 2,500 psm, at least about 3,000 psm, at least about 3,500 psm, at least about 4,000 psm, at least about 4,500 psm, at least about 5,000 psm, at least about 6,000 psm, at least about 7,000 psm, at least about 8,000 psm, at least about 9,000 psm, at least about 10,000 psm). In some embodiments, the density of the nanostructures is less than about 5 to about 10,000 per square micrometer ("psm") (e.g., less than about 5 psm, less than about 25 psm, less than about 50 psm, less than about 75 psm, less than about 100 psm, less than about 150 psm, less than about 200 psm, less than about 250 psm, less than about 300 psm, less than about 350 psm, less than about 400 psm, less than about 450 psm, less than about 500 psm, less than about 600 psm, less than about 650 psm, less than about 700 psm, less than about 750 psm, less than about 800 psm, less than about 850 psm, less than about 900 psm, less than about 950 psm, less than about 1,000 psm, less than about 1,500 psm, less than about 2,000 psm, less than about 2,500 psm, less than about 3,000 psm, less than about 3,500 psm, less than about 4,000 psm, less than about 4,500 psm, less than about 5,000 psm, less than about 6,000 psm, less than about 7,000 psm, less than about 8,000 psm, less than about 9,000 psm, less than about 10,000 psm).

The following examples are included to demonstrate various embodiments of the invention and are not intended to be a detailed catalog of all the different ways in which the present invention may be implemented or of all the features that may be added to the present invention. Persons skilled in the art will appreciate that numerous variations and additions to the various embodiments may be made without departing from the present invention. Hence, the following descriptions are intended to illustrate some particular embodiments of the invention, and not to exhaustively specify all permutations, combinations and variations thereof.

EXAMPLES

Example 1

Titanium Disk Preparation

Ti disks with a diameter of 15 mm were punched from 1 mm thick sheets of grade 2 unalloyed Ti (ASTM F67) and supplied by Institut Straumann AG (Basel, Switzerland). After degreasing the disks in acetone, the disks were exposed to an aqueous solution consisting of 2% ammonium fluoride, 2% hydrofluoric acid and 10% nitric acid at 55° C. for 30 seconds to generate relatively smooth ($S_a$<0.5 μm) pretreatment ("PT") grade 2 titanium disks. A subpopulation of the Pt grade 2 titanium disks was further sandblasted with corundum grit (0.25-0.50 μm) at 5 bar, followed by etching in a solution of hydrochloric and sulfuric acids heated above 100° C. for several minutes (proprietary process of Institut Straumann AG) to produce sand-blasted, large grit and acid etched ("SLA") grade 2 titanium disks. PT grade 2 titanium disks and SLA grade 2 titanium disks were then rinsed with water and sterilized by gamma irradiation at 25 kGy overnight (≥12 h).

Example 2

Hydrothermal Conditions Change the Surface Structures of Titanium Disks

PT grade 2 titanium disks from Example 1 (FIG. 1A) were exposed to acidic (700 mM HCl, 300 mM $H_2SO_4$) or caustic (1 M NaOH) hydrothermal conditions in a Teflon® vessel using a 5 minute ramp to 200° C. for 1 hour. Microwave irradiation (800 W) was used to heat the acidic or caustic solution.

Figure 1:
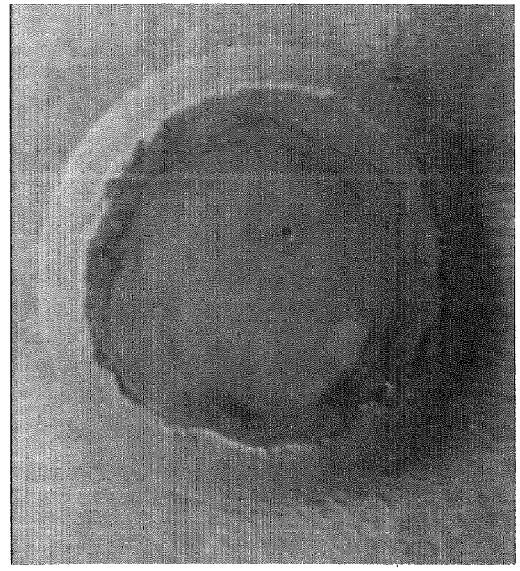
FIG. 1A is a photograph of a PT grade 2 titanium disk.
FIG. 1B is a photograph of acidic (left tube) and caustic (right tube) supernatants following exposure of PT grade 2 titanium disks to an acidic oxidative hydrothermal environment (700 mM HCl, 300 mM $H_2SO_4$ at 200° C. for 1 hour) or a caustic oxidative hydrothermal environment (1 M NaOH at 200° C. for 1 hour).
FIG. 1C is a photograph of a PT grade 2 titanium disk following exposure to an acidic oxidative hydrothermal environment (700 mM HCl, 300 mM $H_2SO_4$ at 200° C. for 1 hour).
FIG. 1D is a photograph of a PT grade 2 titanium disk following exposure to a caustic oxidative hydrothermal environment (1 M NaOH at 200° C. for 1 hour).
Figure 1:
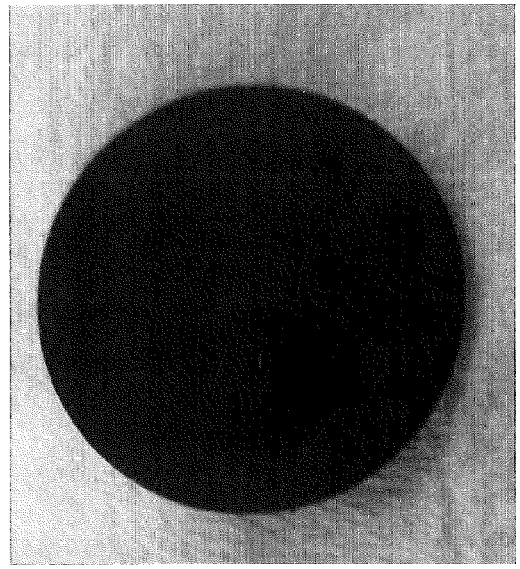
Figure 1:
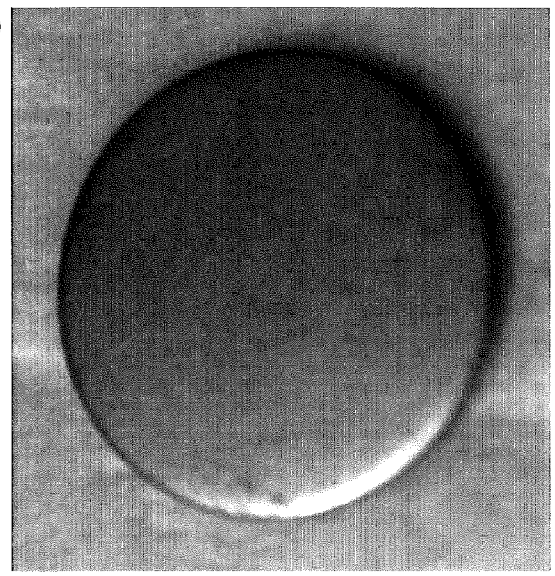
Figure 1:
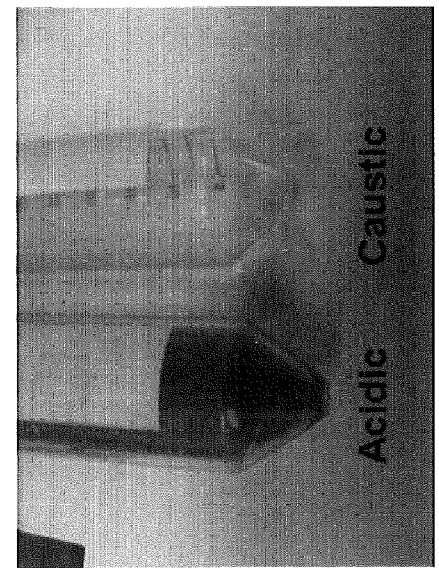
Figure 2:
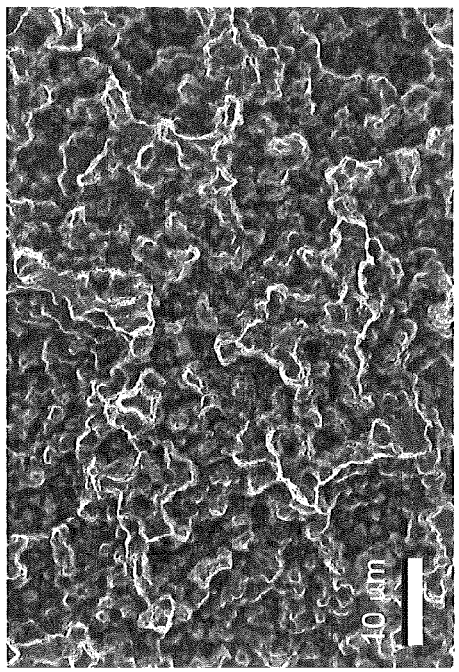
FIGS. 2A-2B are scanning electron microscopy (SEM) images of the surface of a PT grade 2 titanium disk following exposure to an acidic oxidative hydrothermal environment.
FIGS. 2C-2D are SEM images of the surface of a PT grade 2 titanium disk following exposure to a caustic oxidative hydrothermal environment.
Figure 2:
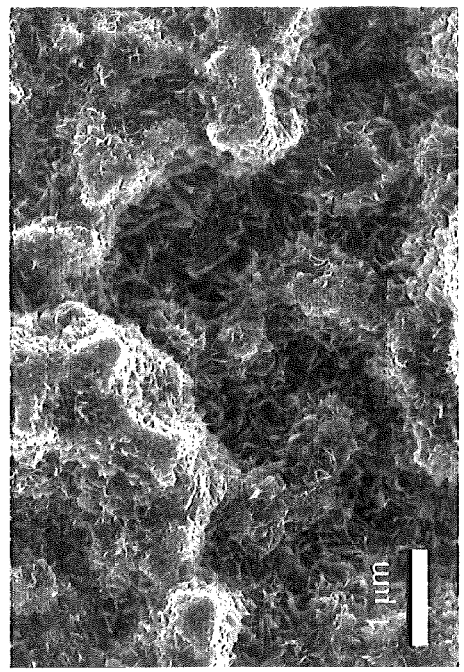
Figure 2:
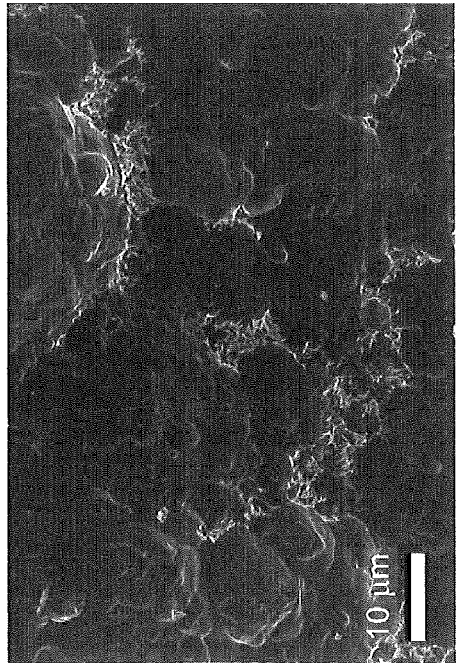
Figure 2:
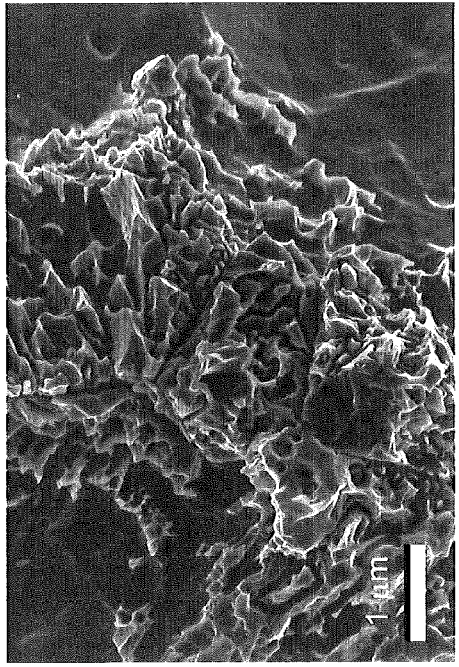

The PT grade 2 titanium disk exposed to acidic hydrothermal conditions (FIG. 1C) was strongly dissolved, as evidenced by its 38% weight loss (0.2686 of 0.7064 grams) and the fact that the acidic solution turned purple (FIG. 1B, left tube). SEM images revealed large hills and valleys in the surface of the disk, but few submicro- or nano-structures (FIGS. 2A-2B).

The PT grade 2 titanium disk exposed to caustic conditions (FIG. 1D) turned black, but exhibited no significant weight loss (0.0001 of 0.7498 grams) and did not appreciably change the color of the caustic solution (FIG. 1B, right tube). SEM images demonstrated that the surface of the disk was completely restructured at the micro-, submicro- and/or nano-scale level (FIGS. 2C-2D).

Other treatments using concentrated acids (e.g., 6 M HCl) resulted in complete dissolution of PT grade 2 titanium disks.

Figure 3:
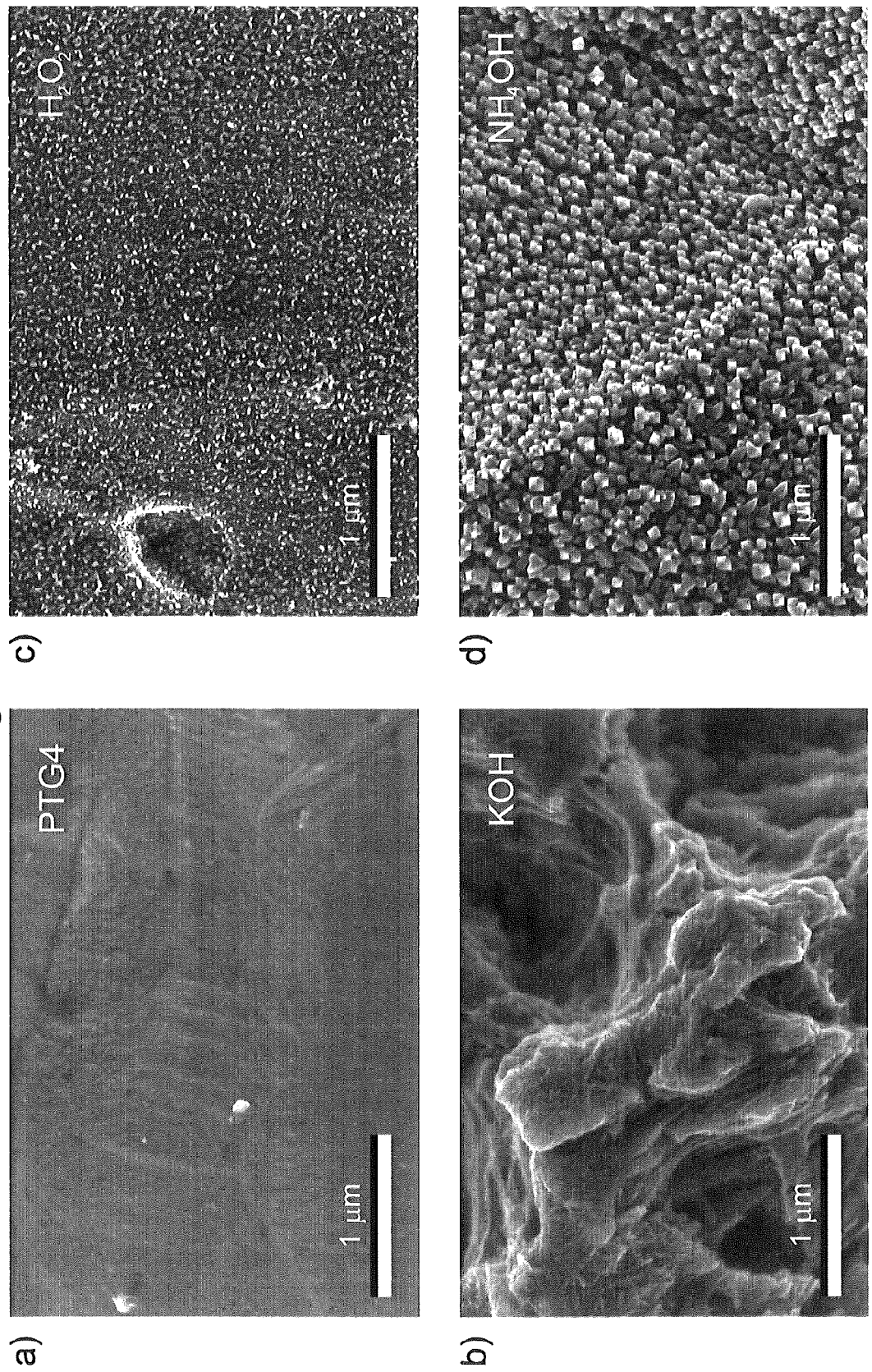
FIG. 3A is an SEM image of the surface of a PT grade 4 titanium disk.
FIG. 3B is an SEM image of the surface of a PT grade 4 titanium disk following exposure to an oxidative hydrothermal environment (1 M KOH at 200° C. for 1 hour).
FIG. 3C is an SEM image of the surface of a PT grade 4 titanium disk following exposure to an oxidative hydrothermal environment (1 M $H_2O_2$ at 200° C. for 1 hour).
FIG. 3D is an SEM image of the surface of a PT grade 4 titanium disk following exposure to an oxidative hydrothermal environment (1 M $NH_4OH$ at 200° C. for 1 hour).

To evaluate the effects of other caustic environments on the development of nanostructures, PT grade 4 titanium disks were exposed to oxidative hydrothermal conditions (1 M KOH, 1 M $H_2O_2$ or 1 M $NH_4OH$) in a Teflon® vessel using a 5 minute ramp to 200° C. for 1 hour. Microwave irradiation (800 W) was used to heat the caustic solutions. As shown in FIG. 3A, the surface of the disks prior to treatment was relatively smooth, with no evident structures except for grain boundaries. Each of the aforementioned hydrothermal treatments changed the color and structures of the disk surface (FIGS. 3B-3D). Hydrothermal treatment with 1 M KOH completely restructured the surface at the micro-, submicro- and/or nano-scale level (FIG. 3B). Hydrothermal treatment with 1 M $H_2O_2$ generated small nanostructures that homogeneously covered the entire surface of the disk without affecting the original microstructure (FIG. 3C). Hydrothermal treatment with $NH_4OH$ generated slightly larger nanostructures than those formed using $H_2O_2$, with high surface coverage and also without affecting the initial microstructure (FIG. 3D).

Figure 4A:
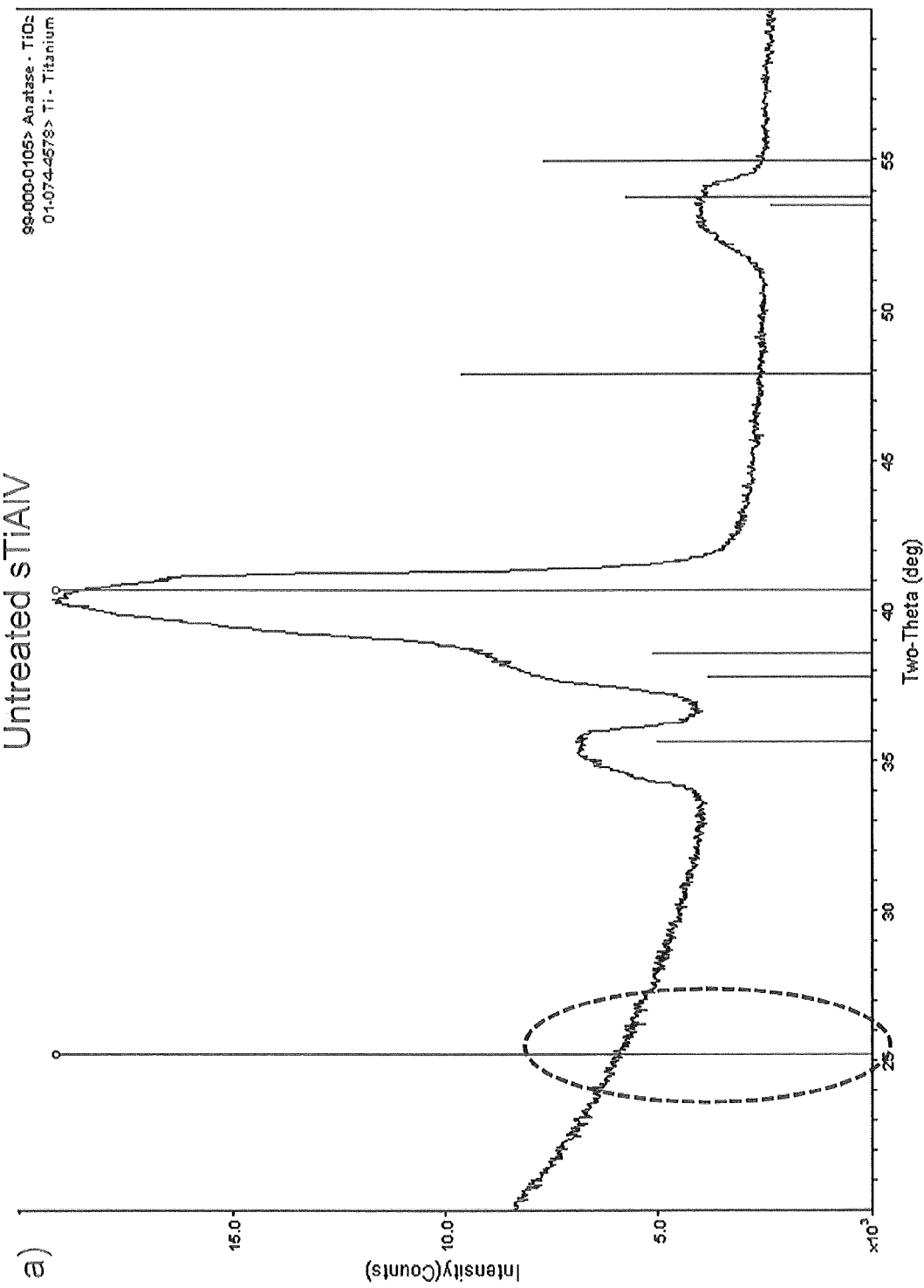
Figure 5A:
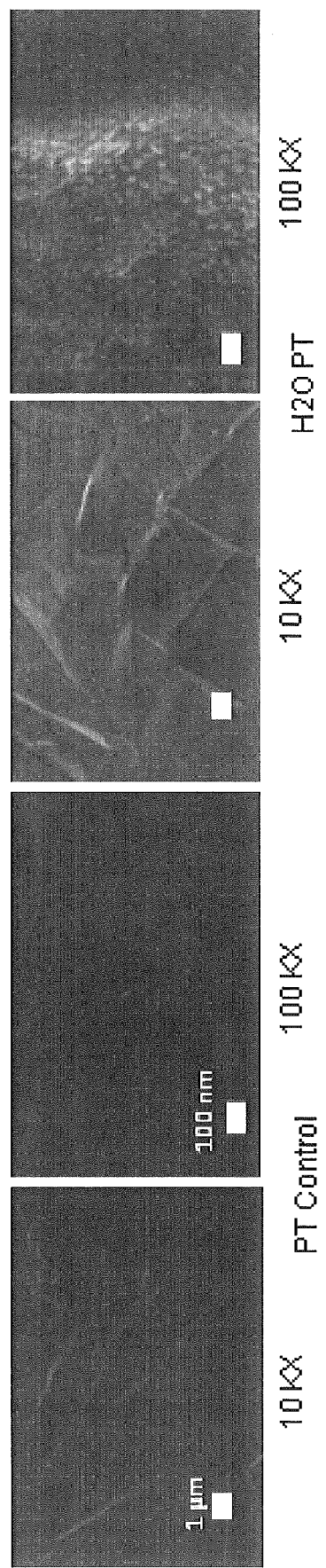
FIG. 5A shows SEM images of the surface a PT grade 2 titanium disk ("PT Control") and the surface of a PT grade 2 titanium disk following exposure to a hydrothermal environment ($H_2O$ at 200° C. for 1 hour; "H2O PT") at 10,000× magnification and 100,000× magnification. Scale bars represent 1 μm at 10,000× magnification and 100 μm at 100,000× magnification.
Figure 5B:
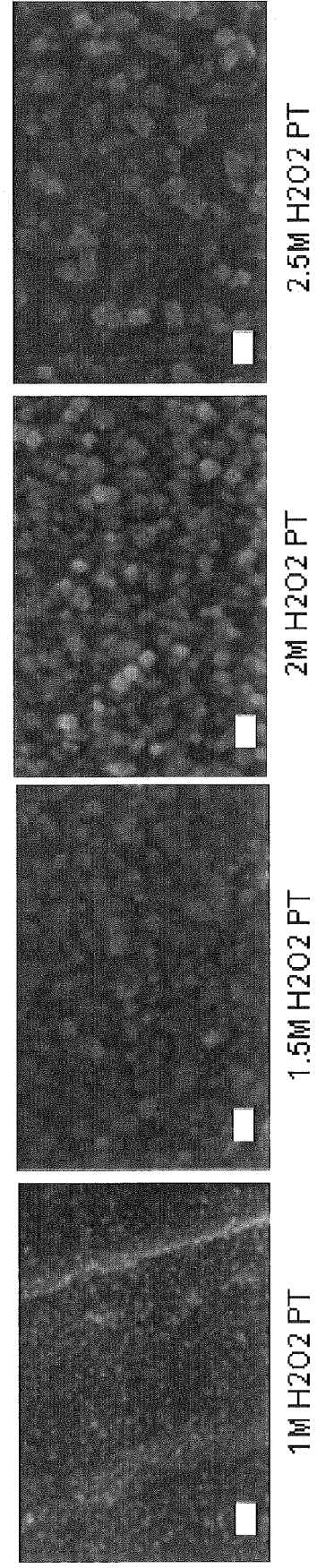
FIG. 5B shows SEM images of the surfaces of PT grade 2 titanium disks following exposure to a different oxidative hydrothermal environments: 1 M $H_2O_2$ at 200° C. for 1 hour ("1 M H2O2 PT"); 1.5 M $H_2O_2$ at 200° C. for 1 hour ("1.5 M H2O2 PT"); 2 M $H_2O_2$ at 200° C. for 1 hour ("2 M H2O2 PT"); and 2.5 M $H_2O_2$ at 200° C. for 1 hour ("2.5 M H2O2 PT"). All images are shown at 100,000× magnification. Scale bars represent 100 μm.
Figure 5C:
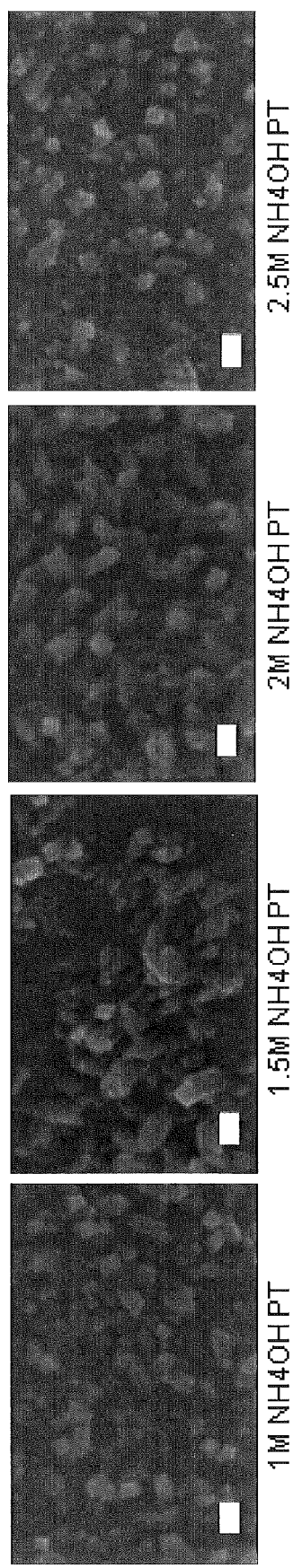
FIG. 5C shows SEM images of the surfaces PT grade 2 titanium disks following exposure to different oxidative hydrothermal environments: 1 M $NH_4OH$ at 200° C. for 1 hour ("1 M NH4OH PT"); 1.5 M $NH_4OH$ at 200° C. for 1 hour ("1.5 M NH4OH PT"); 2 M $NH_4OH$ at 200° C. for 1 hour ("2 M NH4OH PT"); and 2.5 M $NH_4OH$ at 200° C. for 1 hour ("2.5 M NH4OH PT"). All images are shown at 100,000× magnification. Scale bars represent 100 μm.
Figure 5D:
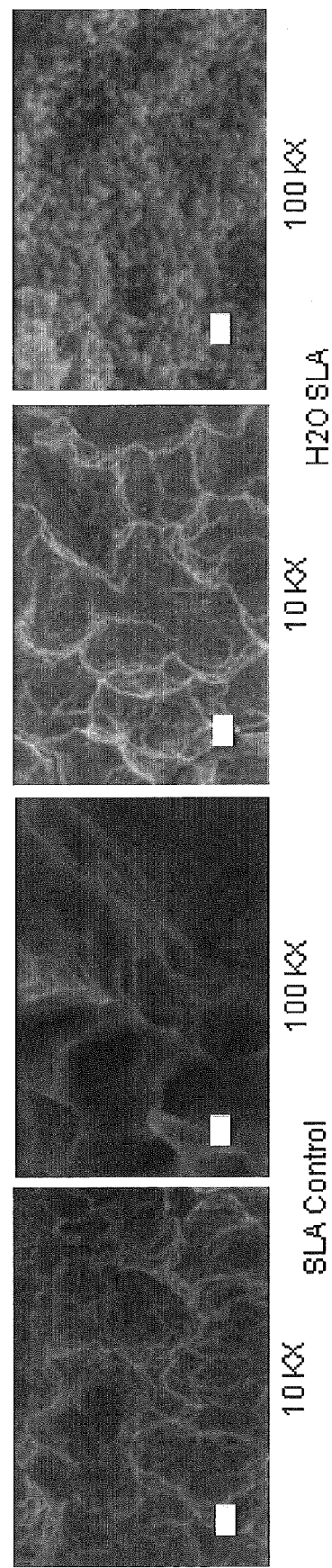
FIG. 5D shows SEM images of the surface of a SLA grade 2 titanium disk ("SLA Control") and the surface of a SLA grade 2 titanium disk following exposure to a hydrothermal environment ($H_2O$ at 200° C. for 1 hour; "H2O SLA") at 10,000× magnification and 100,000× magnification. Scale bars represent 1 μm at 10,000× magnification and 100 μm at 100,000× magnification.
Figure 5E:
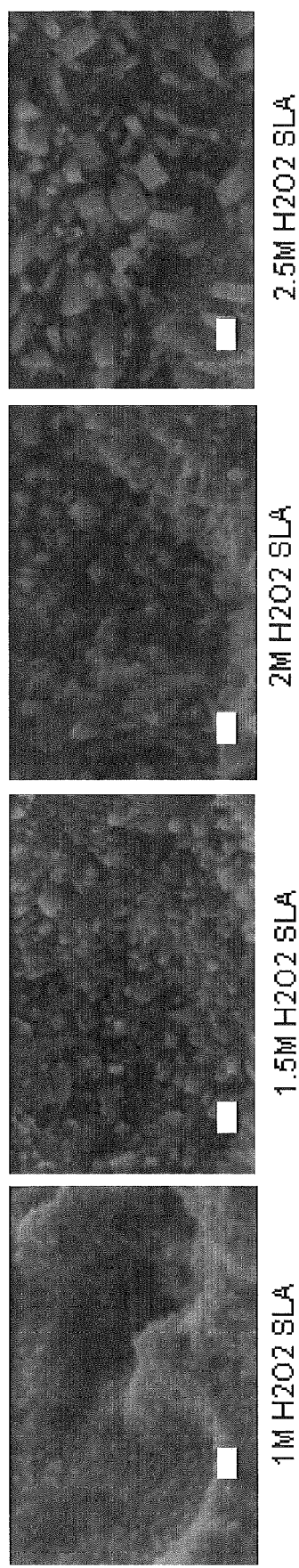
FIG. 5E shows SEM images of the surfaces of SLA grade 2 titanium disks following exposure to different oxidative hydrothermal environments: 1 M $H_2O_2$ at 200° C. for 1 hour ("1 M H2O2 SLA"); 1.5 M $H_2O_2$ at 200° C. for 1 hour ("1.5 M H2O2 SLA"); 2 M $H_2O_2$ at 200° C. for 1 hour ("2 M H2O2 SLA"); and 2.5 M $H_2O_2$ at 200° C. for 1 hour ("2.5 M H2O2 SLA"). All images are shown at 100,000× magnification. Scale bars represent 100 μm.
Figure 5F:
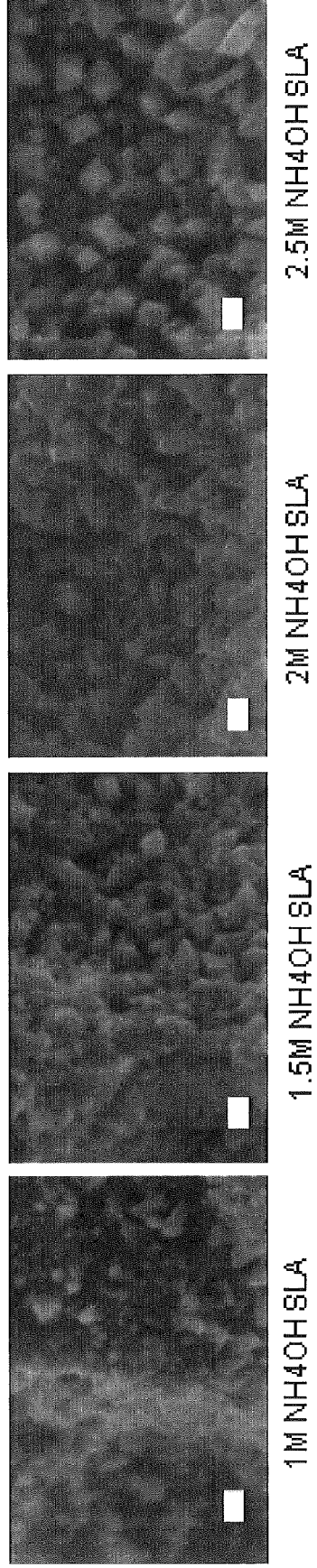
FIG. 5F shows SEM images of the surfaces of SLA grade 2 titanium disks following exposure to different oxidative hydrothermal environments: 1 M $NH_4OH$ at 200° C. for 1 hour ("1 M NH4OH SLA"); 1.5 M $NH_4OH$ at 200° C. for 1 hour ("1.5 M NH4OH SLA"); 2 M $NH_4OH$ at 200° C. for 1 hour ("2 M NH4OH SLA"); and 2.5 M $NH_4OH$ at 200° C. for 1 hour ("2.5 M NH4OH SLA"). All images are shown at 100,000× magnification. Scale bars represent 100 μm.
Figure 6:
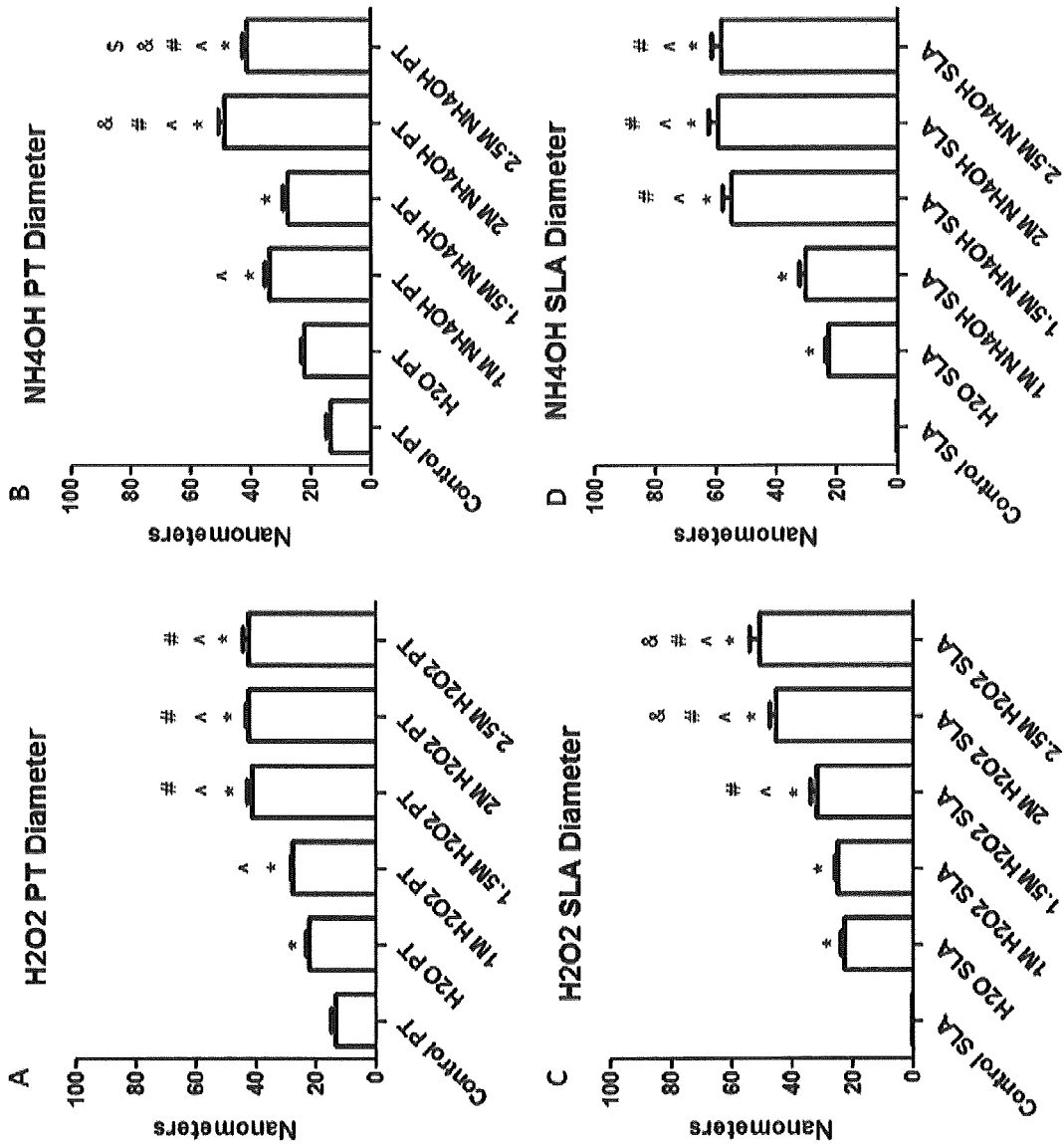
FIG. 6A is a graph showing the mean diameter of the nanostructures on the surfaces of PT grade 2 titanium disks ("Control"), on the surfaces of PT grade 2 titanium disks following exposure to a hydrothermal environment ($H_2O$ at 200° C. for 1 hour; "H2O PT") and on the surfaces of PT grade 2 titanium disks following exposure to different oxidative hydrothermal environments: 1 M $H_2O_2$ at 200° C. for 1 hour ("1 M H2O2 PT"); 1.5 M $H_2O_2$ at 200° C. for 1 hour ("1.5 M H2O2 PT"); 2 M $H_2O_2$ at 200° C. for 1 hour ("2 M H2O2 PT"); and 2.5 M $H_2O_2$ at 200° C. for 1 hour ("2.5 M H2O2 PT"). Standard error is shown for each column. *=statistical significance of $p<0.05$ versus control. ^=statistical significance of $p<0.05$ versus H20 PT. #=statistical significance of $p<0.05$ versus 1 M H2O2 PT.
FIG. 6B is a graph showing the mean diameter of the nanostructures on the surfaces of PT grade 2 titanium disks ("Control"), on the surfaces of PT grade 2 titanium disks following exposure to a hydrothermal environment ($H_2O$ at 200° C. for 1 hour; "H2O PT") and on the surfaces of PT grade 2 titanium disks following exposure to different oxidative hydrothermal environments: 1 M $NH_4OH$ at 200° C. for 1 hour ("1 M NH4OH PT"); 1.5 M $NH_4OH$ at 200° C. for 1 hour ("1.5 M NH4OH PT"); 2 M $NH_4OH$ at 200° C. for 1 hour ("2 M NH4OH PT"); and 2.5 M $NH_4OH$ at 200° C. for 1 hour ("2.5 M NH4OH PT"). Standard error is shown for each column. *=statistical significance of $p<0.05$ versus control. ^=statistical significance of $p<0.05$ versus H20 PT. #=statistical significance of $p<0.05$ versus 1 M NH4OH PT. &=statistical significance of $p<0.05$ versus 1.5 M NH4OH PT. $=statistical significance of $p<0.05$ versus 2 M NH4OH PT.
FIG. 6C is a graph showing the mean diameter of the nanostructures on the surfaces of SLA grade 2 titanium disks ("Control"), on the surfaces of SLA grade 2 titanium disks following exposure to a hydrothermal environment ($H_2O$ at 200° C. for 1 hour; "H2O SLA") and on the surfaces of SLA grade 2 titanium disks following exposure to different oxidative hydrothermal environments: 1 M $H_2O_2$ at 200° C. for 1 hour ("1 M H2O2 SLA"); 1.5 M $H_2O_2$ at 200° C. for 1 hour ("1.5 M H2O2 PT"); 2 M $H_2O_2$ at 200° C. for 1 hour ("2 M H2O2 SLA"); and 2.5 M $H_2O_2$ at 200° C. for 1 hour ("2.5 M H2O2 SLA"). Standard error is shown for each column. *=statistical significance of $p<0.05$ versus control. ^=statistical significance of $p<0.05$ versus H20 SLA. #=statistical significance of $p<0.05$ versus 1 M H2O2 SLA. &=statistical significance of $p<0.05$ versus 1.5 M H2O2 SLA. $=statistical significance of $p<0.05$ versus 2 M H2O2 SLA.
FIG. 6D is a graph showing the mean diameter of the nanostructures on the surfaces of SLA grade 2 titanium disks ("Control"), on the surfaces of SLA grade 2 titanium disks following exposure to a hydrothermal environment ($H_2O$ at 200° C. for 1 hour; "H2O SLA") and on the surfaces of SLA grade 2 titanium disks following exposure to different oxidative hydrothermal environments: 1 M $NH_4OH$ at 200° C. for 1 hour ("1 M NH4OH SLA"); 1.5 M $NH_4OH$ at 200° C. for 1 hour ("1.5 M NH4OH PT"); 2 M $NH_4OH$ at 200° C. for 1 hour ("2 M NH4OH SLA"); and 2.5 M $NH_4OH$ at 200° C. for 1 hour ("2.5 M NH4OH SLA"). Standard error is shown for each column. *=statistical significance of $p<0.05$ versus control. ^=statistical significance of $p<0.05$ versus H20 SLA. #=statistical significance of $p<0.05$ versus 1 M NH4OH SLA. &=statistical significance of $p<0.05$ versus 1.5 M NH4OH SLA. $=statistical significance of $p<0.05$ versus 2 M NH4OH SLA.

Similar results were observed upon exposure of $Ti_6Al_4V$ samples to oxidative hydrothermal conditions (1 M $NH_4OH$ in a Teflon® vessel using a 5 minute ramp to 200° C. for 1 hour). Indeed, x-ray diffraction spectra of modified $Ti_6Al_4V$ samples revealed the presence of anatase crystalline structures on the surface of such samples (FIG. 4B).

Example 3

Hydrothermal Conditions Change the Surface Structures of Titanium Disks

PT grade 2 titanium disks from Example 1 and SLA grade 2 titanium disks from Example 1 were placed individually into Teflon® vessels with 20 mL of $H_2O$, 1.0 M $H_2O_2$, 1.5 M $H_2O_2$, 2.0 M $H_2O_2$, 2.5 M $H_2O_2$, 1.0 M $NH_4OH$, 1.5 M $NH_4OH$, 2.0 M $NH_4OH$ or 2.5 M $NH_4OH$. The Teflon® vessels were heated in a microwave (800 W) for 1 hour at 200° C., with a 5 minute ramp up time and a 5 minute ramp down time.

Following microwave irradiation, the titanium disks were removed from their respective solvents and ultrasonically cleaned, twice for 15 minutes in 2% microsoap and three times for 10 minutes in ultrapure distilled water. Samples were patted dry and covered with a lint-free wipe to continue drying overnight.

Following the aforementioned cleaning processes, the titanium disks were immediately analyzed; stored in air for 3, 14, 28, 56, 83 or 119 days and then analyzed; stored in a saline solution (0.9% w/v of NaCl in $H_2O$) for 3, 14, 28, 56, 83 or 119 days and then analyzed; autoclaved at 121° C. for 30 minutes and then analyzed; autoclaved at 121° C. for 30 minutes, stored in air for 3, 14, 28, 56, 83 or 119 days and then analyzed; sterilized using gamma irradiation (25 kGy overnight) and then analyzed; or sterilized using gamma irradiation (25 kGy overnight), stored in air for 3, 14, 28, 56, 83 or 119 days and then analyzed. Gamma irradiated samples were sent to a gamma irradiation facility for sterilization and were received approximately two weeks after exposure to the oxidative hydrothermal environment and ultrasonic cleaning.

As shown in FIGS. 5A-7E, the surfaces of the titanium disks that were exposed to an oxidative hydrothermal environment exhibited well-defined nanostructures that were not evident on the surfaces of PT grade 2 titanium disks or SLA grade 2 titanium disks prior to exposure to the oxidative hydrothermal environment. Notably, the dimensions and density of the nanostructures appeared to be dependent on the chemistry and the concentration of the solvent. PT grade 2 titanium disks modified in water, 1.0 M $H_2O_2$ or 1.5 M $H_2O_2$ and SLA grade 2 titanium disks modified in water, 1.0 M $H_2O_2$, 1.5 M $H_2O_2$, 2.0 M $H_2O_2$ or 2.0 M $NH_4OH$ exhibited relatively small nanostructures (average diameter=about 10 to about 60 nm) with relatively high and homogeneous surface coverage PT grade 2 titanium disks modified in 2.0 M $H_2O_2$, 2.5 M $H_2O_2$ or 2.5 M $NH_4OH$ also exhibited relatively high surface coverage, with nanostructures that varied more widely in size (average diameter=about 20 to about 60 nm). PT grade 2 titanium disks modified in 1.0 M $NH_4OH$, 1.5 M $NH_4OH$ and 2.5 M $NH_4OH$ and SLA titanium disks modified using 2.5 M $H_2O_2$, 1.0 M $NH_4OH$ or 2.5 M $NH_4OH$ exhibited less surface coverage and more variation in size (average diameter=about 10 to about 60 nm). In particular, PT grade 2 titanium disks modified in 1.5 M $NH_4OH$ exhibited approximately 50% surface coverage with nanostructures having an average diameter of about 40 nm, as well as "nascent" nanostructures in the remaining surface regions that were about 5 to about 12 nm in diameter. SLA titanium disks modified using 2.5 M $H_2O_2$, 1.0 M $NH_4OH$ or 2.5 M $NH_4OH$ exhibited lower surface coverage of nanostructures that was still homogeneous throughout the surface. The surfaces of SLA titanium disks modified in 1.5 M $NH_4OH$ were homogenously covered in nanostructures that were separated by a relative large distance, with nascent nanostructures in between. The emergence of nascent nanostructures was evident on all modified samples except those modified in water. The appearance of nascent nanostructures may be evidence of the constant process of formation and dissolution of surface nanostructures during oxidative hydrothermal treatment.

As shown in FIGS. 8A-8D, the mean contact angles of the nanostructures on the surfaces of PT grade 2 titanium disks and SLA grade 2 titanium disks following exposure to an oxidative hydrothermal environment were significantly lower than those of the corresponding control specimens. This is result is relevant because recent studies have suggested that implant devices with low contact angles may improve osseointegration. See, e.g., Schwarz et al., J. BIOMED. MATER. RES. PART B: APPL. BIOMATER. 88B (2009).

As shown in FIG. 9A, the mean contact angles of the nanostructures on the surfaces of PT grade 2 titanium disks and SLA grade 2 titanium disks following exposure to an oxidative hydrothermal environment and storage for 3, 14, 28, 56, 83 or 119 days suggested that samples became more hydrophobic when stored in air, but remained superhydrophilic when stored in saline solution.

As shown in FIG. 9B, the surface compositions of the surfaces of PT grade 2 disks and SLA grade 2 titanium disks following exposure to an oxidative hydrothermal environment and storage for 3 or 83 days showed changes that occurred during the storage period.

As shown in FIGS. 10A-10D, the surface compositions of the surfaces of PT grade 2 titanium disks and SLA grade 2 titanium disks following exposure to an oxidative hydrothermal environment showed similar levels of carbon, oxygen and titanium regardless of the concentration of the oxidative environment to which they were exposed.

As shown in FIGS. 11A-11B, the surface compositions of the surfaces of PT grade 2 disks and SLA grade 2 titanium disks following exposure to an oxidative hydrothermal environment, different sterilization processes (i.e., No Sterilization, Autoclave and Gamma) demonstrated that the sterilization process selected can impact the surface hydrophilicity and/or chemical composition.

As shown in FIGS. 12A-12B, the mean contact angles and surface compositions of the nanostructures on the surfaces SLA grade 2 titanium disks following exposure to an oxidative hydrothermal environment and storage for 28 or 56 days demonstrated that storage in a saline solution preserves both contact angle and chemical composition, suggesting that storage in saline may be particularly beneficial for long-term storage of surfaces with superhydrophilicity.

As shown in FIGS. 13A-13C, the surfaces of SLA grade 2 titanium disks following exposure to an oxidative hydrothermal environment and storage for 0 or 56 days indicated that storage in a saline solution following hydrothermal modification may promote nanostructure growth on the surface of such samples.

As shown in FIG. 14, the mean pH of the solvents used to modify the surfaces of PT grade 2 titanium disks and SLA grade 2 titanium disks was elevated following exposure to the PT grade 2 titanium disks and SLA grade 2 titanium disks, indicating that the hydrothermal process facilitated the production of hydroxides concurrently with nanostructure formation.

As shown in FIG. 15, the average surface roughness PT grade 2 titanium disks and SLA grade 2 titanium disks following exposure to an oxidative hydrothermal environment indicated that hydrothermal modification did not greatly affect the microstructure of the disks, but significantly increased the average surface roughness of specimens exposed to certain hydrothermal treatments. Microscale surface roughness was evaluated using laser confocal microscopy (LCM). Nanoscale surface roughness was evaluated using atomic force microscopy (AFM).

As shown in FIG. 16, the peak-to-valley differences of PT grade 2 titanium disks and SLA grade 2 titanium disks following exposure to an oxidative hydrothermal environment indicated that hydrothermal treatments using H2O and 1 M H2O2 promoted the formation of large nanofeatures. Peak-to-valley measurements were obtained using AFM.

As shown in FIG. 17, PT grade 2 disks exposed to an oxidative hydrothermal environment at a low temperature developed anatase and rutile crystalline structures.

While the present invention has been particularly shown and described with reference to embodiments thereof, it will be understood by those of ordinary skill in the art that various changes in form and details may be made therein without departing from the spirit and scope of the present invention as defined by the following claims.

That which is claimed:

1. A method of forming nanostructures on a surface of a device, comprising:
exposing the surface of a device having an initial microstructure to an oxidative hydrothermal environment using microwave irradiation, thereby forming nanostructures on the surface of the device;
wherein the average diameter of the nanostructures is about 10 to about 100 nm;
the average height of the nanostructures is about 10 to about 200 nm; and
the mean peak to valley height of the nanostructures is about 1 to about 300 nm; and
wherein the nanostructures are formed without affecting the initial microstructure.

2. The method of claim 1, wherein the device is an implant device.

3. The method of claim 1, wherein the oxidative hydrothermal environment comprises an oxidizing solution.

4. The method of claim 3, wherein the oxidizing solution comprises $H_2O_2$, $H_2O$, and/or $NH_4OH$.

5. The method of claim 3, wherein the oxidizing solution is heated to a target temperature.

6. The. method of claim 5, wherein the target temperature is in the range of about 50 to about 400° C.

7. The method of claim 5, wherein the target temperature is about 200° C.

8. The method of claim 1, wherein the power of the microwave irradiation is in the range of about 100 to about 1,600 W.

9. The method of claim 3, wherein exposing the surface of the device to the oxidative hydrothermal environment comprises submerging the implant device in the oxidizing solution.

10. The method of claim 1, wherein the surface of the device is exposed to the oxidative hydrothermal environment for about 0.1 to about 4 hours.

11. The method of claim 1, wherein the surface of the device is substantially covered in nanostructures following exposure to the oxidative hydrothermal environment.

12. The method of claim 1, wherein the density of the nanostructures is about 5 to about 10,000 per square micrometer.

13. The method of claim 1, wherein the surface of the device is pretreated prior to exposure to the oxidative hydrothermal environment.

14. The method of claim 13, wherein pretreatment of the surface of the device comprises degreasing, pickling, sand blasting, grit blasting, acid etching, machining and/or laser etching.

15. The method of claim 1, wherein the device is a metallic device.

16. The method of claim 1, wherein the device is a ceramic device.

17. The method of claim 1, wherein the device comprises titanium, a titanium alloy and/or titanium dioxide.

18. The method of claim 17, wherein the titanium alloy comprises $Ti_6Al_4V$.

* * * * *

UNITED STATES PATENT AND TRADEMARK OFFICE
CERTIFICATE OF CORRECTION

PATENT NO. : 9,889,229 B2
APPLICATION NO. : 14/362468
DATED : February 13, 2018
INVENTOR(S) : Gittens Ibacache et al.

Page 1 of 1

It is certified that error appears in the above-identified patent and that said Letters Patent is hereby corrected as shown below:

On the Title Page

Item (56) References Cited, Page 2, Right column:
Please correct "Komameni" to read -- Komarneni --

In the Specification

Column 1, after the paragraph, "RELATED APPLICATIONS" and before the heading, "FIELD OF THE INVENTION", please insert the following heading and paragraph:
-- STATEMENT OF FEDERAL SUPPORT
This invention was made with government support under Grant No. AR052102 awarded by the National Institutes of Health. The government has certain rights in the invention. --

In the Claims

Column 25, Line 24, Claim 6:
Please correct "The. method" to read -- The method --

Signed and Sealed this
Twenty-eighth Day of May, 2019

Andrei Iancu
*Director of the United States Patent and Trademark Office*